US006316465B1

(12) United States Patent
Pershadsingh et al.

(10) Patent No.: US 6,316,465 B1
(45) Date of Patent: Nov. 13, 2001

(54) OPHTHALMIC USES OF PPARGAMMA AGONISTS AND PPARGAMMA ANTAGONISTS

(75) Inventors: Harrihar A. Pershadsingh, Bakersfield; Daniel E. Levy, San Carlos, both of CA (US)

(73) Assignee: Photogenesis, Inc., Los Angeles, CA (US)

( * ) Notice: Subject to any disclaimer, the term of this patent is extended or adjusted under 35 U.S.C. 154(b) by 0 days.

(21) Appl. No.: 09/342,381

(22) Filed: Jun. 28, 1999

Related U.S. Application Data

(60) Provisional application No. 60/090,937, filed on Jun. 27, 1998.

(51) Int. Cl.[7] ................................................... A61K 31/41

(52) U.S. Cl. ............................ 514/310; 514/912; 514/914

(58) Field of Search .................................. 514/310, 912, 514/914

(56) References Cited

U.S. PATENT DOCUMENTS

| 5,700,820 | 12/1997 | Vyas et al. ............................. 514/369 |
| 5,817,075 | 10/1998 | Giungo .................................. 604/294 |
| 5,868,728 | 2/1999 | Giungo et al. ......................... 606/1 |

FOREIGN PATENT DOCUMENTS

WO 98/22598    6/1998 (WO) .

OTHER PUBLICATIONS

Arakawa, K., et al., "Novel benzoxazole 2,4–thiazolidinediones as potent hypoglycemic agents, Synthesis and structure–activity relationships." *Chem Pharm Bull* 45(12):1984–1993 (1997).
Barry, Brian W., "Dermatological Formulations", p. 180–187, *Marcel Dekker, Inc.* (New York).
Bazzoni, F., et al., "The Tumor Necrosis Factor Ligand and Receptor Families", *Sem in Med of the Beth Israel Hosp, Boston* 334(26):1717–1725 (1996).
BenEzra, D., et al., "Topical Formulations of Novel Angiostatic Steroids Inhibit Rabbit Corneal Neovascularization", *Investigative Ophthalmology & Visual Science* 38(10):1953–1962 (1997).
Berger, J., et al., "Novel Peroxisome Proliferator–activated Receptor (PRAR) γ AND pparδ Ligands Produce Distinct Biological Effects", *J Biol Chem* 274(10):6718–6725 (1999).
Bissonnette, R. P., et al., "9–cis Retinoic Acid Inhibition of Activation–Induced Apoptosis Is Mediated via Regulation of Fats Ligand and Requires Retioonoic Acid Receptor and Retinoid X Receptor Activation", *Mol Cell Biol* 15(10):5576–5585 (1995).

Braissant, O., et al., "Differential Expression of Peroxisome Proliferator–Activated Receptors (PPARs): Tissue Distribution of PPAR–, –, and –in the Adult Rat", *Endocrinology* 137(1):354–366 (1996).
Braissant, O., et al., "Differential Expression of Peroxisome Proleferator–Activated Receptor–α, –β, and –γ during Rat Embryonic Development", *Endocrinology* 139(6):2748–2754 (1998).
Brown, P. J. et al., "Identification of peroxisome proliferator–activated receptor ligands from a biased chemical library", *Chem Biol* 4(12):909–918 (1997).
Camp, H. S., et al., "PPARγ activators down–regulate the expression of PPARγ in eT3–L1 adipocytes", *Fed Euro Bio Soc* 186–190 (1999).
Camp, H. S., et al., "Regulation of Peroxisome Proliferator–activated Receptor γ Activity by Mitogen–activated Protein Kinase", *J Biol Chem* 272(16):10811–10816 (1997).
Clark, A. F., "Al–3789: a novel ophthalmic angiostatic steroid", *Exp Opin Invest Drugs* 6(12):1867–1877 (1997).
Clark, A. F., et al., "Inhibition of Intraaocular Tumor Growth by Topical Application of the Angiostatic Steroid Anecortave Acetate", *IOVS* 40(9):2158–2162 (1999).
Clark, A. F., et al., "Ocular angiostatic agents", *Exp Opin Ther Patents* 20(4):427–448 (2000).
Cobb, J. E., et al., "N–(2–Benzoylphenyl)–L–tyrosine PPARγ Agonists. 3. Structure—Activity Relationship and Optimization of the N–Aryl Substituent", *J Med Chem* 41:5055–5069 (1998).
Collins, J. L., et al., "N–(2–Benzoylphenyl)–L–tyrosine PPARγ Agonist. 2. Structure—Activity Relationship and Optimization of the Phenyl Alkyl Ether Moiety", *J Med Chem* 41: 5037–5054 (1998).

(List continued on next page.)

*Primary Examiner*—Jose' G. Dees
*Assistant Examiner*—Michael A. Williamson
(74) *Attorney, Agent, or Firm*—Brinks, Hofer, Gilson & Lione

(57) ABSTRACT

Methods of treating diseases of ocular tissues expressing the nuclear receptor PPARγ, by inhibiting the inflammatory response, the neovascularization and angiogenesis, and programmed cell death (apoptosis) in these target tissues, comprising administering to a human or animal in need of treatment an effective amount of a compound that modifies the activity of PPARγ, or pharmaceutically acceptable salts and solvates thereof.

Novel compounds and methods for their synthesis are provided, including a compound having the general structure:

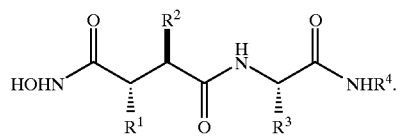

12 Claims, No Drawings

OTHER PUBLICATIONS

Cursiefen, C., et al., "Angiogenesis in Corneal Diseases: Histophathologic Evaluation of 254 Human Corneal Buttons with Neovascularization", *Cornea* 17(6):611–613 (1998).

DeFaller, J. M., et al., "A New Pharmacological Treatment for Angiogenesis", *Pterygium*, 12:159–181 (2000).

Elstner, E., "Ligands for peroxisome proliferator–activated receptor γ and retinoic acid receptor inhibit growth and induce apoptosis of human breast cancer cells in vitro and in BNX mice", *Proc Natl Acad Sci USA* 95:8806–8811 (1998).

Forman, B.M., "15–Deoxy–$\Delta^{12,14}$ $_{13}$ Prostaglandin $J_2$ Is a Ligand for the Adipocyte Determination Factor PPARγ", *Cell* 83:803–812 (1995).

Fujimura, S., et al., "Effects of troglitazone on the growth and differentiation of hemotopoietic cell lines", *Int J Oncol* 13:1263–1267 (1998).

Geng, Y., et al., "Caspase–3–induced gelsolin fragmentation contributes to actin cytoskeletal collapse, nucleolysis, and apoptosis of vascular smooth muscle cells exposed to proinflammatory cytokines", *Eur Journ Cell Bio* 77:294–302 (1998).

Giorgini, A.E., "Troglitazone Exhibits Immunomodulatory Activity on the Cytokine Production of Activated Human Lymphocytes", *Horm Metab Res* 31:1–4 (1999).

Havener, William H., "Ocular Pharmacology", *The C. V. Mosby Company, St. Louis*, MO (1983).

Henke, B.R., et al., "N–(2–Benzoylphenyl)–L–tyrosine PPARγ Agonists. I. Discovery of a Novel Series of Potent Antihyperglycemic and Antihyperlipidemic Agents", *J Med Chem* 41:5020–5035 (1998).

Heusch, W. L., et al., "Effects of bombesin of methadone–induced apoptosis of human lung cancer cells", *Cancer Letters* 136:177–185 (1999).

Hulin, B., et al., "Hypoglycemic Activity of a Series of α–Alkylthio and α–Alkoxy Carboxylic Acids Related to Ciglitazone", *J Med Chem* 39:3897–3907 (1996).

Iantosca, M. R., et al., "Bone Morphogenetic Proteins–2 and –4 Attenuate Apoptosis in a Cerebellar Primitive Neuroectodermal Tumor Cell Line", *J Neurosci Res* 56:248–258 (1999).

Jiang, C., et al., "PPAR–agonists inhibit production of monocyte inflammatory cytokines", *Nature* 39:82–86 (1998).

Kitamura, Y., et al., "Increased Expression of Cyclooxygenases and Peroxisome Proliferator–Activated Receptor–γ in Alzheimer's Disease Brains", *Biochem and Biophysic Res Comm* 254:582–586 (1999).

Kliewer, S. A., "Fatty acids and eicosanoids regulate gene expression through direct interactions with peroxisome proliferator–activated receptors α and γ", *Proc Natl Acad Sci USA* 94:4318–4323 (1997).

Kliewer, S. A., et al., "The nuclear receptor PPARγ—bigger than fat", 576–581 (1998).

Kliewer, S. A., et al., "A Prostaglanding $J_2$ Metabolite Peroxisome Proliferator–Activated Receptor γ and Promotes Adipocyte Differentiation", *Cell* 83:813–819 (1995).

Kurtz, T. W., et al., "Transcription–Modulating Drugs. A New Frontier in the Treatment of Essential Hypertension", *Dept of Lab Med and Med Univ of Cal SF*, 380–386 (1998).

Lehmann, J. M., et al., An Antidiabetic Thiazolidinedione Is a High Affinity Ligand for Peroxisome Proliferator–activated Receptor (PPAR ), *J Biol Chem* 270:12953–12956 (1995).

Lejeune, F.J., "Clinical applications of TNF–alpha in cancer", *Cur Opin Immunol* 10:573–580 (1998).

Lemberger, T., et al., "PPAR Tissue Distribution and Interactions with Other Hormone–Signaling Pathways$^{a}$", *Ann NY Acad Sci* 804:231–251 (1996).

Levy, D. E., et al., "Matix Metalloproteinase Inhibitors: A Structure—Activity Study", *J Med Chem* 41:199–223 (1998).

Li, X., et al., "Two Auronols from *Pseudolarix amabilis*", *J Nat Prod* 62:767–769 (1999).

Lohray, B. B., et al., "Novel Euglycemic and Hypolipidemic Agents. 1", *j Med Chem* 41:1619–1630 (1998).

Mancuso, A. J., et al., "Activated Dimethl Sulfoxide: Useful Reagents for Syntheses", *Synthesis*, 165–185 (1981).

Mangelsdorf, D.J., et al., "The RXR Heterodimers and Orphan Receptors", *Cell* 83:841–850 (1995).

McNatt, L. G., et al., "Angiostatic Activity of Steroids in the Chick Embryo CAM and Rabbit Cornea Models of Neovascularization", *Journal of Ocular Pharmacology and Therapeutics* 15(5):413–423 (1999).

Mitra, A. K., "Ophthalmic Drug Delivery Systems", *Marcel Dekker, Inc.*, New York, NY (1993).

Mueller, E., et al., "Terminal Differentiation of Human Breast Cancer through PPAR ", *Mol Cell* 1:465–470 (1998).

Mukherjee, R., "Identification, Characterization, and Tissue Distribution of Human Peroxisome Proliferator–activated Receptor (PPAR) Isoforms PPARγ2 versus PPARγ1 and Activation with Retinoid X Receptor Agonists and Antagonists", *J Biol chem.*, 272(12):8071–8076 (1997).

Natoli, G., "Apoptotic, Non–apoptotic, and Anti–apoptotic Pathways of Tumor Necrosis Factor Signalling", *Biochem Pharmacol* 56:915–920 (Jan. 1998).

Oberfield, J.L., et al., "A Peroxisome proleferator–activated receptor ligand inhibits adipocyte differentiation", *Proc Natl Acad Sci USA* 96:5102–5106 (1999).

Ohsumi, J., et al., "Troglitazone Prevents the Inhibitory Effects of Inflammatory Cytokines on Insulin–Induced Adipocyte Differentiation in 3T3–L1 Cells", *Endocrinology* 135(5):2279–2282 (1994).

Pan, D., et al., "The Cytotoxic Principles of *Pseudolarix kaempferi*: Pseudolaric Acid–A and –B and Related Derivatives", *Planta Med* 56:383–385 (1990).

Pershadsingh, H.A., et al., "Ocular Diseases and Peroxisome Prolifertor–Activated Receptor–γ (PPARγ) in Mammalian Eye", *Proc Soc Neursci* 25:2193 (1999).

Pershadsingh, H. A., "Pharmacological peroxisome proliferator–activated receptorγ ligands: emerging clinical indications beyond diabetes", *Exp Opin Invest Drugs* 8(11):1859–1872 (1999).

Ricote, M., et al., "The peroxisome proliferator–activated receptor–γ is a negative regulator of macrophage activation", *Nature* 391:79–82 (1998).

Schulman, I.G., et al., "Transactivation by Retinoid X Receptor–Peroxisome Proliferator–Activated Receptor γ(PPARγ) Heterodimers: Intermolecular Synergy Requires Only the PPARγ Hormone–Dependent Activation Function", *Mol Cell Biol* 18:3483–3494 (1998).

Spencer, N., et al., "Constitutive activation of NF–κB in an animal model of aging", *Intl Immunol* 9(10):1581–1588 (1997).

Spiegelman, B.M., "PPAR-γ: Adipogenic Regulator and Thiaxolidinedione Receptor", *Diabetes* 47:507–514 (1998).

Tamatani, M., "Tumor Necrosis Factor Induces Bcl-2 and Bcl-x Expression through NFκB Activation in Primary Hippocampal Neurons", *J Biol chem.* 274(13):8531–8538 (1999).

Tontonoz, P., et al., "Terminal differentiation of human liposarcoma cells induced by ligands for peroxisome proliferator–activated receptor and the retinoid X receptor", *Proc Natl Acad Sci USA* 94:237–241 (1997).

Wang, X., et al., "Suppression of NF-κB—Dependent Proinflammatory Gene Expression in Human RPE Cells by a Proteasome Inhibitor", *IOVS* 40(2):477–486 (1999).

Xin, X. et al., "Peroxisome Proliferator–activated Receptor Ligands Are Potent Inhibitors of Angiogenesis in Vitro and in vivo", *J Biol Chem* 274(13):9116–9121 (1999).

Yang, X. Y., et al., "Activation of Human T Lymphocytes is Inhibited by Peroxisome Proliferator–activated Receptor γ (PPARγ) Agonists", *J Biol Chem* 275(7):4541–4544 (2000).

OPHTHALMIC USES OF PPARGAMMA AGONISTS AND PPARGAMMA ANTAGONISTS

This application claims benefit to U.S. provisional application Ser. No. 60/090,937, filed Jun. 27, 1998.

FIELD OF THE INVENTION

The present invention is directed to the administration of drugs for the treatment of ophthalmic disorders. In one aspect, the present invention is directed to the administration of drugs which acts as ligands to modulate the activity of peroxisome proliferator-activated receptors to either treat proliferative and/or inflammatory diseases of the eye or to ameliorate or prevent degenerative diseases of the eye. In another aspect, the present invention is directed to novel compounds, and methods for making same, which can be used in the treatment of proliferative and/or inflammatory diseases of the eye and/or to ameliorate or prevent degenerative diseases of the eye.

BACKGROUND OF THE INVENTION

The peroxisome proliferator-activated receptor-γ (PPARγ), a nuclear gene transcription factor, modulates the expression of genes involved in the regulation of growth and differentiation in a variety of cell types that express the receptor. PPARγ is a member of the class II family of nuclear hormone receptors which include the ligand-activated nuclear hormone transcription factors which encode the steroid, vitamin D and thyroid hormone and retinoid nuclear receptors (Mangelsdorf D J, Evans R M. Cell 1995;83:841–850). PPARγ exists as at least two isotypes, PPARγ 1 and PPARγ 2. Throughout this writing PPARγ refers to any of these isotypes or combination thereof. PPARγ 2 is expressed selectively in adipose tissue, whereas PPARγ 1 is expressed at lower levels in a variety of other rodent and human tissues (Spiegelman B M. Diabetes 1998;47:507–514).

Without limiting the present invention to any particular theory of operation, it is believed that activation of PPARγ modulates the expression of genes containing the appropriate peroxisome proliferator response element in its promoter region. PPARγ can be activated by naturally occurring nutrients such as polyunsaturated fatty acids and hormone-like arachidonic acid derivatives, and by synthetic ligands such as the antidiabetic thiazolidine-2,4-diones (Lehmann J M et al. J Biol Chem. 1995; 270:12953–12956) and N-(2-benzoylphenyl)-L-tyrosine derivatives (Henke B R et al. J Med Chem 1998; 41:5020–36). Binding of thiazolidinediones to PPARγ causes receptor activation which induces changes in the transcriptional activity of genes that down-regulate and inhibit the activity of inflammatory cytokines, and promote differentiation by inhibiting proliferation. Conversely, binding of certain ligands to PPARγ can have the opposite effect, i.e. oppose differentiation (Oberfield J L et al. Proc Natl Acad Sci USA 1999; 96:6102–6). A search for endogenous PPARγ ligands identified prostaglandin J2 (PG J2) and its metabolites as PPARγ activators, with 15-deoxy-Δ-12,14-PG J2 being the most potent inducer of adipogenesis. However, the thiazolidinediones had the highest affinities for PPARγ; relative affinities for various thiazolidinediones are known, for example in descending order: rosiglitazone (BRL 49653)>pioglitazone>troglitazone>15-deoxy-Δ-12,14-PG J2 >15-deoxy-PG J2) (Forman B M et al. Cell 1995;83:803–12; Kliewer S A et al. Cell 1995;83:813–819).

The precise mechanism whereby ligand activation of PPARγ leads to changes in gene expression is poorly understood. Full activation of PPARγ requires its functional dimerization with the retinoid X receptor (RXR). Alterations in the conformation of the PPARγ/RXR heterodimer induced by RXR and PPARγ specific ligands may regulate gene transcription in opposing ways, depending on the nature of the ligand and its interaction with the binding domain on PPARγ (Mangelsdorf D J, Evans R M. Cell 1995;83:841–850). PPAR/RXR heterodimers can be activated independently by ligands for RXR as well as by ligands for PPARγ, or they may have a synergistic or augmented effect with dual activation (Schulman I G, et al. Mol Cell Biol. 1998; 18:3483–494). The endogenous ligand for RXR is 9-cis-retinoic acid. Nutrient retinoids such as all-trans retinoic acid are converted to 9-cis retinoic acid by a ubiquitous intracellular isomerase (Schulman I G, et al. Mol Cell Biol. 1998; 18:3483–494). The full spectrum of genes that can be regulated by PPARγ remains to be defined.

PPARγ agonists have been shown to inhibit the production of TNF-α and other inflammatory cytokines by human macrophages (Jiang C-Y et al. Nature 1998; 391:82–86) and T lymphocytes (Giorgini A E et al. Horm Metab Res 1999; 31:1–4). They also inhibit proliferation and promote differentiation of breast cancer and liposarcoma cells (Mueller E et al. Mol Cell 1998; 1:465–470; Tontonoz P et al. Proc Natl Acad Sci USA 1997; 94:237–241). More recently, the natural PPARγ agonist 15-deoxy-Δ-12,14-PG J2, has been shown to inhibit neovascularization and angiogenesis (Xin X et al. J Biol Chem. 1999; 274:9116–9121) in the rat cornea. Spiegelman et al., in Patent Cooperation Treaty application number PCT/US97/22879, published Jun. 18, 1998, disclose methods for inhibiting proliferation of PPARγ-responsive hyperproliferative cells by using PPARγ agonists; numerous PPARγ agonists are disclosed by Spiegelman et al., as well as methods for diagnosing PPARγ-responsive hyperproliferative cells. All documents referred to herein are incorporated by reference as if reproduced in full below. It is difficult to predict what cells and diseases are influenced by PPAR activity due to the unpredictability of PPAR expression in cells, and due to the lack of understanding of PPAR activity mechanisms. Further, PPAR is expressed in some cells while in a normal state, but not expressed or expressed to a lesser degree by the abnormal cells, or visa versa (in other words, PPAR is differentially expressed in diseased versus normal cells). For example, the present inventor has discovered that PPARγ is expressed in normal human keratinocytes but not in normal human dermal fibroblasts.

SUMMARY OF THE INVENTION

This invention is based in part on the surprising discovery that PPARγ is expressed to different degrees in the various tissues of the eye. For example, PPARγ is expressed in some but not all layers of the retina. It is confined to certain layers of the cornea, is strongly expressed in the choriocapillaris and modestly in the uveal tract. Finally, PPARγ is strongly expressed in the conjunctival epidermis and intraocular muscles but not in the ciliary muscle (Pershadsingh et al., "Ocular Diseases And Peroxisome Proliferator-Activated Receptor (PPARγ) In Mammalian Eye," Proc Soc Neurosci 1999, in press).

Methods of this invention include the treatment of inflammatory, proliferative, dystrophic and/or degenerative ocular diseases, such as those involving ischemia, angiogenesis, neovascularization, and/or apoptosis, by administering to a human or animal in need of treatment an effective amount of a PPARγ ligand (i.e. a PPARγ agonist or a PPARγ antagonist) to slow, reverse, or stop the disorder. The PPARγ agonist may be administered alone or in combination with a RXR ligand, a retinoid or vitamin A derivative, a flavonoid, a glucocorticoid, an androgen, an estrogen, a non-steroidal anti-inflammatory agent, a vitamin D derivative, an anti-infective agent, a protein kinase C inhibitor, a MAP kinase inhibitor, an antioxidant, an anti-apoptotic agent, a growth factor, a nutrient vitamin, an unsaturated fatty acid, or an arachidonic acid derivative.

In a preferred embodiment, suitable ligands are selected from the group consisting of a thiazolidine compound, arachidonic acid, an arachidonic acid metabolite (e.g., prostaglandin J2 or its metabolites), an hydroxamic acid derivative, a N-(2-benzoylphenyl)-L-tyrosine derivative, and a phenylacetic acid derivative. In another aspect, the present invention comprises treatment of ophthalmic disorders using matrix metalloproteinase inhibitors, some of which have PPARgamma agonist activity and antioxidant activity. A further aspect of the present invention involves novel compounds, their synthesis, and use in the treatment of ophthalmic disorders. In one aspect, the present invention is directed to the making of a compound having the general structure A set forth below:

STRUCTURE A

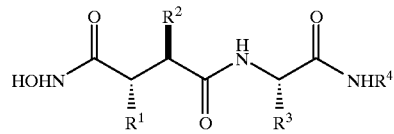

wherein $R^1$ is OH, $OXR^6$, OY, or

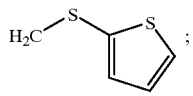

$R^2$ is $C_1$–$C_8$ alkyl, aryl, alkaryl or arylalkyl where aryl groups are defined as substituted or unsubstituted phenyl, biphenyl, naphthyl or pyridyl groups; $R^3$ is $CH_2R^5$, $C_1$–$C_8$ alkyl, aryl, alkaryl or arylalkyl where aryl groups are defined as substituted or unsubstituted phenyl, biphenyl, naphthyl or pyridyl groups; $R^4$ is H, $XR^6$, or Y; $R^5$ is the residue of a naturally occurring amino acid;

$R^6$ is

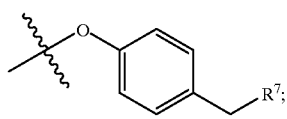

$R^7$ is

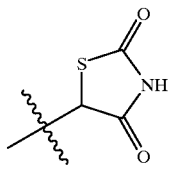

or

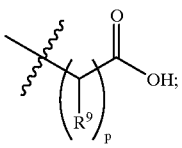

$R^9$ is

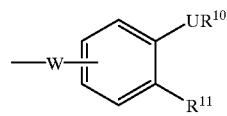

or —W-$R^{17}$; $R^{10}$ is $(CH_2)_q$—$R^{12}$, $NH_2$, NHMe, $NMe_2$, $OR^{18}$, $(C_3$–$C_8)$cycloalkyl, or unsubstituted, monosubstituted or disubstituted Ar; $R^{11}$ and $R^{13}$ are either hydrogen or combine to form a single bond or, alternately, $R^{13}$ is U and $R^{11}$ forms a direct link with U to form a single bond;

$R^{12}$ is either

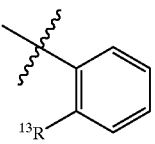

$R^{14}$, $R^{15}$ and $R^{16}$ are independently hydrogen, $CF_3$, $(C_1$–$C_6)$ alkyl, $(C_1$–$C_6)$alkoxy, Ar or Ar—$(CH_2)_t$—O—; $R^{17}$ is unsubstituted, monosubstituted or disubstituted Ar; $R^{18}$ is hydrogen or $(C_1$–$C_6)$alkyl; each U is independently $CH_2$, CHOH, C=O, O, S, SO, $SO_2$, C=N—$NH_2$; W is O, S, NH, or $CH_2$; X is —$(CH_2)_n$—or —$(CH_2)_n$—NY—$(CH_2)_o$—;

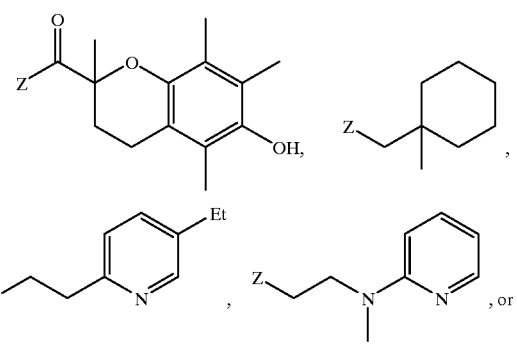

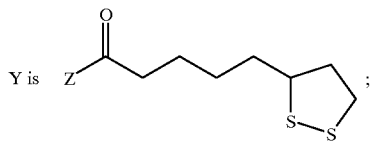

Z is a direct link, A—(CH$_2$)$_n$—NH—, or A—(CH$_2$)$_n$—O—; A is a direct link; n=2–10; o=2–10; p is an integer from 0 to 1; q is an integer from 0 to 6; and t is an integer from 1 to 6; wherein if R$_1$ is H then R$_4$ is XR$_6$ where X is —(CH$_2$)$_n$—NY—(CH$_2$)$_o$—; if R$_1$ is Y then R$_4$ is XR$_6$ where X is —(CH$_2$)$_n$—; if R$_4$ is H then R$_1$ is XR$_6$ where X is —(CH$_2$)$_n$—NY—(CH$_2$)$_o$—and if R$_4$ is Y then R$_1$ is XR$_6$ where X is —(CH$_2$)$_n$—. Preferred embodiments of the present invention include the following thiazolidinediones, which are referred to as Example 1, Example 2, Example 3, and Example 4:

Example 1

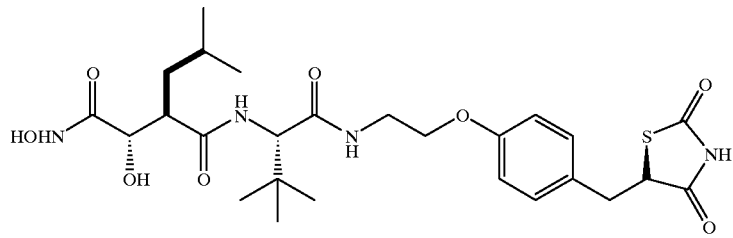

Example 2

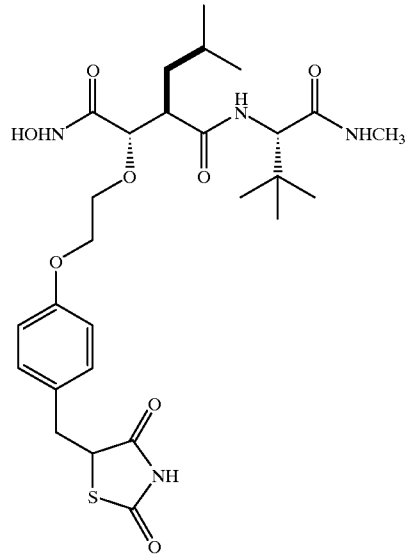

Example 3

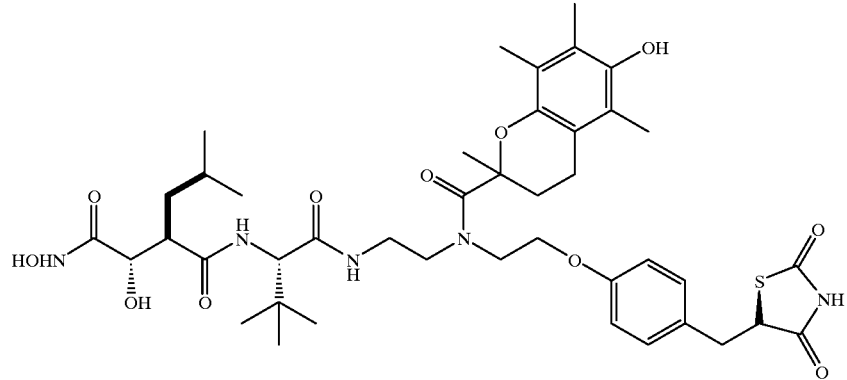

-continued

Example 4

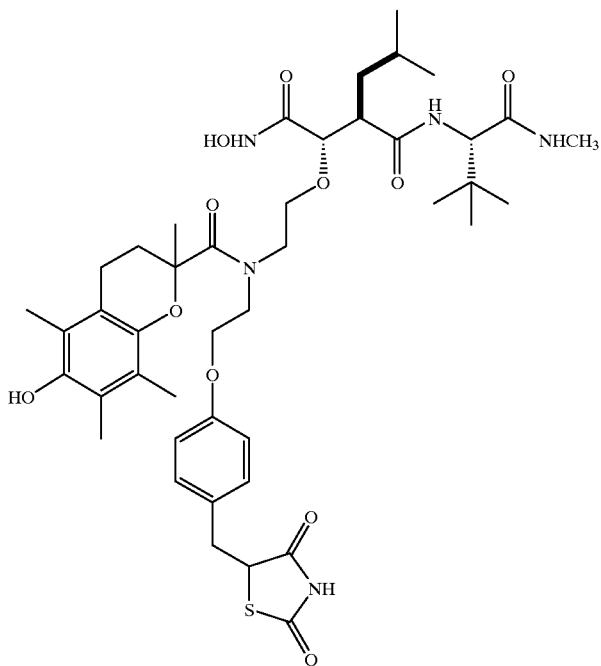

Synthetic Schemes for the synthesis of each of these compounds are presented separately under the corresponding title. The present invention also includes methods for use of a compound having the general structure A for the treatment of an ophthalmic disorder, and in a preferred embodiment, at least one of the compounds selected from Example 1, Example 2, Example 3, and Example 4 is administered in an effective amount to a mammal, or a human in particular, in need thereof, for the treatment of an ophthalmic disorder.

Another aspect of the present invention relates to the protection of cells against apoptosis (which for example includes the premature apoptotic death of photoreceptor cells in retinal dystrophies such as retinitis pigmentosa). In one aspect, this involves the local or systemic application of nuclear receptor regulating proteins having histone acetyltransferase activity. Examples of these proteins include cyclic-AMP response element binding protein (CREB), CREB binding protein (CBP), p300/CBP, and steroid receptor coactivators (SRCs), e.g. SRC-1, as well as synthetic compounds that activate histone acetyltransferase. These substances may be delivered by direct local application or intraocularly, or incorporated within inactivated viral vectors, e.g. adenovirus, and the vector delivered by direct local application or intraocularly (e.g. subretinally or intravitreously) by invasive device. These therapies may be used in conjunction with PPARγ, RXR and/or RAR ligands.

DETAILED DESCRIPTION OF THE INVENTION

In the most extensive studies on its tissue distribution in the central nervous system, PPARγ was found to be weakly expressed in the inner and outer nuclear layers, and barely detectable in the ganglion cells of the rat retina (Braissant, O. et al. Endocrinology 1996; 137:354–366; Lemberger T et al. Ann N Y Acad Sci 1996; 804:231–251; Mukherjee, R. J Biol Chem 1997; 272:8071–8076; Braissant, O. et al. Endocrinology. 1998; 139:2748–2754). We have recently extended these observations and surprisingly demonstrated the heterogenous expression of PPARγ in other layers of the retina and in several ocular tissues of the rat other than the retina, including the conjunctiva, cornea, uveal tract, intraocular muscles and choriocapillaris (Pershadsingh et al.1999 Proc Soc Neurosci, in press). This heterogeneous distribution of PPARγ expression among tissues of the eye is surprising, unexpected, and unpredictable.

This invention is based in part on the unexpected finding that PPARγ is expressed in certain ocular tissues to a much greater extent than others (in some cases PPARγ has not been detected at significant levels). Immunofluorescence histochemical studies revealed that PPARγ is strongly expressed in retinal photoreceptor outer nuclear layer and outer segments, the outer plexiform layer, the retinal pigmented epithelium, the choriocapillaris, the corneal epithelium and endothelium, and to a lesser extent, the retinal photoreceptor inner nuclear layer and inner segments, and tissues of the uveal tract (iris and ciliary body) (See Pershadsingh et al., supra, in press).

This invention relates in one aspect to diseases of the eye involving ocular tissues that express PPARγ, and more particularly to new methods for treating ophthalmologic disorders which include: inflammatory diseases, proliferative diseases, vitreoretinopathies and uveitis, hereditary and non-hereditary degenerative diseases, diseases resulting from hypoxia or vascular ischemia, diseases involving angiogenesis and neovascularization, age-related degenerative diseases such as those associated with diabetes, ischemia and aging, and degenerative and dystrophic diseases involving premature apoptosis, such as retinopathies and retinal dystrophies. A non-limiting example of a preferred embodiment is a treatment retinitis pigmentosa in which an effective amount of a PPARgamma antagonist is administered to a patient suffering from and/or at risk for retinitis pigmentosa to reverse, slow, stop, and/or prevent vision loss associated therewith. The methods of the present invention also relate to the treatment of diseases of ocular tissues regardless of etiological agent. For example, the treatment of corneal injury or ulceration caused by unrelated etiological agents: 1) foreign body (e.g. contact lens), infectious agent (e.g. chlamydia trachomatis, cytomegalovirus or human immunodeficiency virus), physical agent (e.g. UV radiation), chemical agent (e.g. acids, caustic solvents) chronic systemic disease (e.g. collagen vascular diseases). Methods of the present invention for treating these diseases comprise in a preferred embodiment the administration to a human or animal in need of treatment, an effective amount of any natural or synthetic substance that modifies the activity of PPARγ.

PPARγ forms a functional heterodimer with RXR which, in turn, dimerizes with other nuclear receptors, namely, the retinoic acid receptor, the vitamin D receptor and the steroid receptors (including the nuclear receptors for androgens, estrogens, glucocorticoids, and mineralocorticoids). Thus, there is potential for cross-talk between PPARγ and these nuclear receptors through RXR, the master regulator of ligand-dependent nuclear transcription, via the PPARγ/RXR heterodimer. In this regard, another aspect of the invention is the use of PPARγ ligands in combination with a glucocorticoid (e.g. prednisolone, prednisone), a mineralocorticoid (e.g. dehydroepiandrostenedione), an estrogen (e.g. estrodiol), an androgen (e.g. testosterone) retinoic acid derivatives (e.g. 9-cis-retinoic acid, 13-trans-retinoic acid, all-trans retinoic acid) and/or a vitamin D derivative (e.g. calcipotriol, calcipotriene) for the treatment of the ophthalmic disorders set forth herein.

1. Methods for Inhibiting Inflammation in PPARγ-Expressing Cells

In one aspect, this invention delineates methods for preventing or inhibiting inflammatory diseases involving ocular tissues by treatment with a PPARγ ligand. In general the method involves systemic delivery or local application of an amount of a PPARγ ligand to inhibit the expression of genes encoding inflammatory cytokines such as such as tumor necrosis factor-α (TNF-α), or inhibition of the production of inflammatory cytokines such as IL-1α, IL-1β, IL-2, IL-6, IL-8, and TNF-α, or the inhibition of their biological activity. The method also includes systemic delivery or local application of an amount of the PPARγ ligand to effect inhibition of the activity of the pro-inflammatory nuclear receptor NF-κB, and to inhibit the ability of NF-κB to induce the expression of genes that encode inflammatory cytokines. While the PPARγ agonist can be utilized alone, the subject anti-inflammatory therapy can be utilized in combination with other therapeutics such as steroidal and non-steroidal anti-inflammatory agents, RXR agonists and agents that modulate apoptosis in pathological cells.

In one embodiment of the invention, the cells to be treated are those involved in intraocular inflammations. These include inflammatory (immune system) cells (e.g. T lymphocytes and macrophages), PPARγ-expressing cells and tissues involved in the pathogenesis of inflammatory ocular diseases, including all forms of uveitis and uveoretinitis, iritis, cyclitis, choroiditis, chorioretinitis, vitritis, keratitis and conjunctivitis. Other aspects of this invention includes treatment of inflammatory diseases of the described cells and tissues caused by diverse etiological agents or pathologies, including foreign bodies such as contact lens, infectious agents such as bacteria (e.g. Treponema pallidum, Mycobacterium tuberculare, Borelia burgdorferi, ricketsia ricketsiae) viruses (e.g. cytomegalovirus or human immunodeficiency virus, herpes simplex virus), fungi (Candida sp., Cryptococcus neoformans, coccidioides immitis, histoplasma casulatum), parasites (e.g. Toxoplasma gondii, Pneumocystis carnii), physical agents (e.g. UV radiation), chemical agents (e.g. acids, alkalis, caustic solvents), systemic autoimmune disorders (e.g. type 1 diabetes mellitus, sjogren's syndrome and hyperthyroidism), and collagen vascular diseases (e.g. ankylosing spondylitis, rheumatoid arthritis, lupus erythematosus, Reiter syndrome, Bechet disease, ulcerative colitis, Crohn's disease, Wegener's granulomatosis). Additional examples of inflammatory ophthalmological diseases that relate to this invention are shown in Table 1.

2. Methods of Inhibiting Neovascularization and Angiogenesis in PPARγ-Expressing Cells In another aspect, this invention includes methods for preventing or inhibiting proliferative ocular diseases involving angiogenesis and neovascularization by treatment with a PPARγ ligand. Neovascularization in the adult animal is usually a pathological process, and is in direct contradistinction to non-pathological neovascularization which usually occurs in normal embryogenesis (e.g., development of the embryonic vascular system). In this embodiment, neovascularization refers specifically to the pathological neovascularization.

In general the method involves systemic delivery or local application of an amount of a PPARγ ligand to inhibit the proliferation of cells (e.g. endothelial and vascular smooth muscle cells), and cellular processes (e.g. expression of the proliferative phenotype) that lead to development of abnormal capillaries that constitute the pathological neovascular lesions. The method also includes systemic delivery or local application of an amount of the PPARγ ligand to inhibit the production and/or the activity of mitogenic and angiogenic growth factors, in particular vascular endothelial growth factor, basic fibroblast growth factor and platelet-derived growth factor, as these substances are inappropriately produced and have abnormal (pathological) effects on the PPARγ-expressing cells or tissues involved in neovascularization.

In one embodiment of the invention, a PPARγ ligand is delivered systemically or applied locally to prevent or treat diseases involving neovascularization of ocular tissues. Neovascular diseases of the retina include hyperproliferative retinopathies, vitreoretinopathies and retinal degeneration associated with systemic diseases such as diabetes mellitus, ischemic and hypoxic conditions associated with retinal vein and artery occlusion (e.g. from sickle cell disease or thrombosis), retinal degeneration resulting from retinal detachment, and age-related macular degeneration. It is to be understood that in one aspect of the present invention, the term PPARγ ligand may be used to describe compounds which may provide the claimed beneficial action, depending on the disease being treated, by acting as a PPARγ agonist, as a PPARγ antagonist, or as neither a PPARγ agonist, or PPARγ antagonist. In another aspect, novel compounds of the present invention may act as matrix metalloproteinase inhibitors (MMPI) for the treatment of ophthalmic disorders such as those set forth herein.

Contact lenses, especially the hard variety, can cause irritation resulting in inflammation, hypoxemia and ultimately neovascularization resulting in blindness and the need for corneal transplantation. Moreover, corneal transplantation and corneal injury from any cause can lead to neovascularization. Effective pharmacological treatment of corneal neovascularization could reduce the need for corneal transplantation (Cursiefen C et al. Cornea 1998; 17:611–613).

3. Methods for Inhibiting Apoptosis in PPAR-γ Expressing Cells

In yet another aspect, this invention delineates methods for preventing or inhibiting programmed cell death (also called apoptosis), as a means for treating hereditary and non-hereditary degenerative retinopathies and retinal dystrophies. In general the method involves systemic delivery or local application of an amount of the PPARγ ligand to prevent or inhibit inappropriate and pathological apoptosis and eventual death of photoreceptor cells in these diseases, resulting in permanent and irreversible blindness.

Activation of PPARγ with the ligand troglitazone, induces apoptosis in human HL-60 acute promyelocytic leukemia cells (Fujimura S et al. Int J Oncol 1998; 13:1263–1267) and in human monocyte-derived macrophages (Chinetti et al. J. Biol. Chem 1998; 273:25573–25580). Whereas activation of PPARγ with troglitazone alone or other PPARγ agonists reversibly inhibits clonal growth of cultured human MCF-7 breast cancer cells, the combination of troglitazone with all-trans retinoic acid synergistically and irreversibly inhibits growth and induces apoptosis of MCF-7 cells in vitro and in BNX mice in vivo (Elstner E et al. Proc Natl Acad Sci USA 1998; 95:8806–8811). It is surprising that in vitro troglitazone, alone or in combination with all-trans retinoic acid, had no effect on normal, non-malignant cells taken from the contralateral uninvolved breast of patients with breast cancer (Elstner E et al. Proc Natl Acad Sci USA 1998; 95:8806–8811).

The mechanisms involved in apoptotic cell death and protection of cells from apoptotic cell death are not understood. In fact, TNF-" signalling pathways have been implicated both in apoptosis (cell death) and protection from apoptosis (cell survival) (see Natoli G, et al. Biochem Pharmacol. 1998; 56:915–920 for a review of these concepts). For example, TNF-" and nuclear factor-6B activation have been shown to be associated with anti-apoptosis and the survival of hippocampal neurons (Tamatani M, et al. J Biol Chem 1999; 274:8531–8538). On the other hand, TNF-" has been reported to induce apoptosis in both cancer cells (Lejeune F J et al. Curr Opin Immunol 1998; 10:573–580) and non-cancer cells (Geng Y J et al. Eur J Cell Biol 1998; 77:294–302). Moreover, the PPARγ activator troglitazone, which has an apoptotic effect on cancer cells when administered with 9-cis-retinoic acid, inhibits the expression and production of TNF-", and 9-cis-retinoic acid has been shown to inhibit cytokine-induced apoptosis (Bissonnette RP et al. Mol Cell Biol 1995; 15:5576–5585). Consequently, it was impossible to predict whether activation or inhibition of PPARγ will result in an apoptotic or an anti-apoptotic effect.

A method of this invention relates in part to the surprising discovery of the presence of varying concentrations of PPARγ in varying ophthalmic cells, and the anti-apoptotic effect of PPARγ ligands that serves to protect cells from premature death and promote their survival, as in degenerative and dystrophic diseases, e.g. photoreceptor cells retinitis pigmentosa, and retinal neural and glial cells in diabetic retinopathy and both "wet" (exudative) and "dry" (aereolar) age-related macular degeneration. One aspect of this invention relates to the systemic or local administration of PPAR γ activating ligands such as thiazolidinediones, N-(2-benzoylphenyl)-L-tyrosine derivatives, phenylacetic acid derivatives, or prostaglandin metabolites or derivatives, to treat these diseases. Another aspect involves the administration of PPARγ antagonist ligands to treat these diseases.

Structural studies have revealed that agonist ligands activate the PPARγ through direct interactions with the C-terminal region of the ligand-binding domain, which includes the activation function 2 helix. In a preferred embodiment, N-carboxyphenyl substituted, 5 diarylacetamide substituted, 4-thiazolidineones are utilized by administration of an effective amount to a patient in need thereof to treat retinal disorders, which by way of non-limiting example of preferred embodiments include retinitis pigmentosa, and age-related macular degeneration. A preferred compound for this use is 4-(4-(4-carboxyphenyl) butyl)- 2-heptyl-4-oxo-5-thiazolidine, of which a preferred chiral compound is known as GW0072 and whose structure and synthesis is reported by Glaxo Wellcome of Research Triangle Park, North Carolina, USA (see Oberfield J L et al. Proc Natl Acad Sci USA 1999; 96:6102–6). X-ray crystallography revealed that GW0072 occupied the ligand-binding pocket by using different epitopes than the known PPARγ agonists and did not interact with the activation function 2 helix. Therefore, it is possible to synthesize a library of compounds designed to occupy the PPARγ ligand-binding pocket by using different epitopes that do not interact with the activation function 2 helix.

This establishes an approach to the design of PPARγ ligands with modified biological activities, one of which is the prevention of apoptosis. Thus, a method of this invention for treating degenerative retinal dystrophies that result in pathological, premature apoptosis, is the systemic delivery or local application of an amount of the PPARγ antagonist to inhibit apoptosis thereby preventing premature cell death. Examples of these diseases are shown in Table 2.

PPARγ modulators include a diverse variety of naturally occurring and synthetic compounds, and may be administered alone or in combination with a retinoic acid derivative, a carotenoid, a phytol metabolite, a vitamin D derivative, a natural or synthetic antioxidant compound, a vitamin or nutrient. The present invention encompasses treatment of the diseases listed in Tables 1, 2 and 3. Examples of naturally occurring retinoids include 9-cis-retinoic acid, all-trans-retinoic acid, phytol metabolites (e.g. phytannic acid) a carotenoid vitamin A precursor (e.g. β-carotene), and other vitamin A derivatives. Examples of natural antioxidants include ascorbic acid (vitamin C), vitamin E and the tocopherol isoforms, α-lipoic acid, flavones (e.g. quercetin), flavonones, isoflavones (e.g. genistein), flavonols, catechins, epicatechins, anthocyanidins, proanthocyanidins, and terpenes. Specifically, a method of this invention involves the use of a PPARγ ligand in combination with a retinoid X receptor (RXR) ligand or a retinoic acid receptor (RAR) ligand, wherein the PPAR ligand is an agonist or an antagonist, the RXR ligand is an agonist or an antagonist, and the RAR ligand is an agonist or an antagonist. Examples of PPARγ agonists and antagonists have been provided in the foregoing. Examples of RXR ligands include, but are limited to 9-cis-retinoic acid, BMS649 (Bristol-Myers Squibb), LGD1069 (Targretin), LG100268, tazarotene, Ro 25–6603 (Hoffman La Roche) TTNPB ((E)-4-[2-5,5,8,8-tetramethyl-5,6,7,8-tetrahydro—2-naphtylenyl)-1-propenyl]benzoic acid and phytannic acid. Examples of RAR ligands include, but are limited to 9-cis-retinoic acid, all-trans retinoic acid, tazarotene, etretinate acitretin, BMS753, BMS61, BMS 961 (Bristol-Meyers Squibb compounds), Ro 40–6055 (Hoffman La Roche). Some compounds, such as 9-cis-retinoic acid, are high affinity ligands of both RXR and RAR.

Naturally occurring ligands that modify the activity of PPARγ, include arachidonic acid derivatives or metabolites such as eicosanoids (e.g. various isomeric forms of 8-hydroxytetraenoic acid) and cyclopentenone prostaglandins (e.g. prostaglandins in the J and A series and their metabolites), and polyunsaturated fatty acids. Diterpene acids and auronols (e.g. pseudolaric acids A and B) isolated from *Pseudolarix kaempferi* (Pan D J et al. Planta Med 1990; 56:383–385; Li X C et al. J Nat Prod 1999; 62:767–769) have recently been shown to activate PPARγ (Feller D et al. personal communication) and are expected to be useful in the practice of this invention.

Synthetic ligands that modify the activity of PPARγ, antidyslipidemic fibrates (e.g. clofibrate, fenofibrate, benzofibrate, ciprofibrate, gemfibrozil), thiazolidine derivatives (e.g. thiazolidinediones), oxazolidine derivatives (e.g. oxazolidinediones), alpha-alkylthio, alpha-alkoxy and carboxylic acid derivatives of thiazolidines and oxazolidines (Hulin B et al. J Med Chem 1996; 39:3897–3907), N-(2-L-tyrosine derivatives (Henke B R et al. J Med Chem 1998; 41:5020–5036; Collins JL et al. J Med Chem 1998; 41:5037–5054; Cobb J E et al. J Med Chem 1998; 41:5055–5069), phenyl acetic acid derivatives (Berger J et al. J. Biol. Chem. 1999; 274:6718–6725), and indole-thiazolidinedione derivatives (Lohray B B et al. J Med Chem 1998; 41:1619–1630. Specific examples of thiazolidinediones for use in this invention include: troglitazone, pioglitazone, rosiglitazone (formerly BRL 49653), ciglitazone, englitazone, darglitazone. A method for synthesizing libraries of biased compounds designed to activate PPARγ and its isotypes e.g. PPARδ) has been published, and can be used to create novel modulators (e.g. agonists) of PPARγ (Brown P J et al. Chem Biol 1997; 4:909–918).

The methods of treatment included in one aspect of this invention are practiced by administering to a human in need thereof a dose of a compound (or pharmaceutically acceptable salts and solvates thereof in acceptable pharmaceutical excipients) that modifies the activity of PPARγ. The terms "modify and modulate" are defined to include its usually accepted meaning and includes treating a human subject prophylactically to alter inflammation, apoptosis, proliferation, immune function, and expression of oncogenes and other genes controlling cell metabolism. The present method includes both medical therapeutic and/or prophylactic treatment, as necessary.

How to Use the Invention

The methods of treatment provided by this invention are practiced by administering to a human or vertebrate animal in need a dose of a compound, or a pharmaceutically acceptable salt or solvate thereof, that modifies the activity of PPARγ. In another aspect, the novel compounds set forth under the general structure A, and in another preferred embodiment, at least one of the the compounds selected from the group consisting of Example 1, Example 2, Example 3, and Example 4, is administered to treat an ophthalmic disorder, which in one aspect is due to matrix metalloproteinase activity, and in another aspect is administered to treat an inflammatory and/or proliferative ophthalmic disease. The specific diseases and associated disorders that can be treated with the compounds described in this invention are listed in Tables 1, 2 and 3. Using a method of the invention, therapeutic compounds are typically administered to human patients topically (extraocular application), intraocularly (by chemical delivery system or invasive device), or systemically (e.g. oral or other parenteral route). Parenteral administration is used in appropriate circumstances apparent to the practitioner. Preferably, the compositions are administered in unit dosage forms suitable for single administration of precise dosage amounts.

To prepare a topical formulation for the treatment of ophthalmological disorders listed in Tables 1, 2 and 3, a therapeutically effective concentration of the compound is placed in a dermatological vehicle as is known in the art. The amount of the therapeutic compound to be administered and the compound's concentration in the topical formulations depend upon the vehicle, delivery system or device selected, the clinical condition of the patient, the side effects and the stability of the compound in the formulation. Thus, the physician employs the appropriate preparation containing the appropriate concentration of the therapeutic compound and selects the amount of formulation administered, depending upon clinical experience with the patient in question or with similar patients.

The therapeutic compound is optionally administered topically by the use of a transdermal therapeutic system (see Barry, Dermatological Formulations, (1983) p. 181 and literature cited therein). While such topical delivery systems have been designed largely for transdermal administration of low molecular weight drugs, by definition they are capable of percutaneous delivery. They may be readily adapted to administration of the therapeutic compounds of the invention by appropriate selection of the rate-controlling microporous membrane.

For ophthalmic applications the therapeutic compound is formulated into solutions, suspensions, and ointments appropriate for use in the eye. The concentrations are usually as discussed above for topico-local preparations. For ophthalmic formulations, see Mitra (ed.), Ophthalmic Drug Delivery Systems, Marcel Dekker, Inc., New York, N.Y. (1993) and also Havener, W. H., Ocular Pharmacology, C.V. Mosby Co., St. Louis (1983).

The concentration of the therapeutic compound used depends on the mode of delivery. For topical ocular and extraocular formulations, the concentration of the therapeutic compound is in the range of about 0.01% weight/weight (w/w) to about 10% w/w. Typically, the concentration of the therapeutic compound for this mode of delivery is in the range of about 0.025% w/w to about 2.5% w/w. Solid dispersions of the therapeutic compound as well as solubilized preparations can be used. For intraocular formulations (chemical delivery or delivery by invasive device), the therapeutic compound is delivered at a concentration high enough to achieve a final concentration in the range of about 0.1 $\mu$mol/L to about 10 $\mu$mol/L within the target ocular compartment (e.g. the posterior chamber for the treatment of retinal diseases). Typically, for this mode of delivery, the final concentration of the therapeutic compound is in the range of about 0.25 $\mu$mol/L to about 5 $\mu$mol/L. Solid dispersions of the therapeutic compound as well as solubilized preparations can be used. Thus, the precise concentration is subject to modest but not undue experimental manipulation well within the skill of the ordinary medical practitioner in order to optimize the therapeutic response. Suitable vehicles include oil-in-water or water-in-oil emulsions for preparation of ointments using mineral oils, petrolatum, lanolin, glycerin and the like as well as gels such as hydrogel.

A preferred embodiment of the present invention involves administration of semi-solid or solid implants containing PPARgamma agonists, PPARgamma antagonists, the novel compounds of the present invention, N-carboxyphenyl substituted, 5 diarylacetamide substituted, 4-thiazolidineones (e.g., 4-(4-(4-carboxyphenyl)butyl)-2-heptyl-4-oxo-5-thiazolidine), and/or other drugs, which may be in slow release form, directly into the subretinal space. This may be accomplished in a preferred embodiment by using instrumentation and techniques described in U.S. Pat. Nos. 5,817,075 and 5,868,728.

For oral administration, either solid or fluid unit dosage forms can be prepared. For preparing solid compositions such as tablets, the compound of interest is mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound of interest with an inert pharmaceutical diluent and filling the mixture into a hard gelatin capsule of appropriate size. Soft gelatin capsules are prepared by machine encapsulation of a slurry of the compound of interest with an acceptable vegetable oil, light liquid petrolatum or other inert oil. Fluid unit dosage forms for oral administration such as syrups, elixirs and suspensions can be prepared. The water soluble forms can be dissolved in an aqueous vehicle together with sugar, aromatic flavoring agents and preservatives to form a syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate formulations for parenteral use are apparent to the practitioner of ordinary skill. Usually, the therapeutic compound is prepared in an aqueous solution (discussed below) in a concentration of from about 1 to about 100 mg/ml. More typically, the concentration is from about 10 to 60 mg/ml or about 20 mg/ml. Concentrations below 1 mg/ml may be necessary in some cases depending on the solubility and potency of the compound selected for use. The formulation, which is sterile, is suitable for various topical or parenteral routes including intra-dermal, intramuscular, intravascular, and subcutaneous.

In addition to the therapeutic compound, the compositions may include, depending on the formulation and mode of delivery desired, pharmaceutically-acceptable, non-toxic carriers or diluents, which include vehicles commonly used to form pharmaceutical compositions for animal or human administration. The diluent is selected so as not to unduly affect the biological activity of the combination. Examples of such diluents which are especially useful for injectable formulations are water, the various saline, organic or inorganic salt solutions, Ringer's solution, dextrose solution, and Hank's solution. In addition, the pharmaceutical composition or formulation may include additives such as other carriers; adjuvants; or nontoxic, nontherapeutic, nonimmunogenic stabilizers and the like.

Furthermore, excipients can be included in the formulation. Examples include cosolvents, surfactants, oils, humectants, emollients, preservatives, stabilizers and anti-oxidants. Any pharmacologically acceptable buffer may be used, e.g., tris or phosphate buffers. Effective amounts of diluents, additives and excipients are those amounts which are effective to obtain a pharmaceutically acceptable formulation in terms of solubility, biological activity, etc.

The term "unit dosage form" refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals. Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described.

Thus, a composition of the invention includes a therapeutic compound which may be formulated with conventional, pharmaceutically acceptable, vehicles for topical, oral or parenteral administration. Formulations may also include small amounts of adjuvants such as buffers and preservatives to maintain isotonicity, physiological and pH stability. Means of preparation, formulation and administration are known to those of skill. See generally Remington's Pharmaceutical Science 15th ed., Mack Publishing Co., Easton, Pa. (1980).

Slow Release Delivery

Slow or extended-release delivery systems, including any of a number of biopolymers (biological-based systems), systems employing liposomes, colloids, resins, and other polymeric delivery systems or compartmentalized reservoirs, can be utilized with the compositions described herein to provide a continuous or long term source of therapeutic compound. Such slow release systems are applicable to formulations for delivery via topical, intraocular, oral, and parenteral routes.

Delivery by Invasive Device

As mentioned above, delivery to areas within the eye, in situ can be accomplished by injection, cannula or other invasive device designed to introduce precisely metered amounts of a desired formulation to a particular compartment or tissue within the eye (e.g. anterior or posterior chamber, uvea or retina). Preferably, a solid or semisolid implant can be delivered subretinally using the instrumentation and methods described in U.S. Pat. Nos. 5,817,075 and 5,868,728.

Routes of Administration

Therapeutic agents of the invention are usually delivered or administered topically for treating disorders involving the eye that are listed in Tables 1, 2 and 3. Oral administration is preferred for disorders in Tables 1, 2 and 3 that cannot be treated effectively by topical therapy. Additionally, the agents can be delivered parenterally, especially for treatment of retinitis and degenerative retinal diseases, and for other conditions in Tables 1, 2 and 3, that do not respond to oral or topical therapy, or for conditions where oral or topical therapy is not feasible. Parenteral therapy is typically intraocular, transcutaneous, intradermal, intrathecal, intramuscular or intravenous.

A preferred way to practice the invention for disorders in Tables 1, 2 and 3 to which this method is applicable, is to apply the compound of interest, in a cream, lotion, ointment, or oil based carrier, directly to the lesion. Typically, the concentration of therapeutic compound in a cream, lotion, or oil is 0.1 to 2.5%. In general, the preferred route of administration is oral, topical, intraocular or parenteral. Topical administration is preferred in treatment of lesions of the external eye as in keratitis, conjunctivitis, scleritis, squamous cell carcinoma where such direct application is practical and clinically indicated.

Oral administration is a preferred alternative for treatment of other lesions discussed in Tables 1, 2 and 3, where direct topical application is not useful as in the treatment of retinitis and other retinal degenerative diseases. Intravenous administration may be necessary in disorders that cannot be effectively treated by topical or oral administration.

Intraocular and transcutaneous injections or other invasive technique are preferred alternative in cases where the practitioner wishes to treat one or a few specific areas or lesions depending on their location within the eye. Usually, the compound is delivered in an aqueous solution. Additionally, the therapeutic compounds are injected directly into lesions (intra-lesion administration) in appropriate cases. Intradermal administration is an alternative for extraocular lesions. Intra-lesional and intradermal injections are alternative routes of application for certain lesions, e.g. extraocular neoplastic or hyperplastic lesions such as squamous cell carcinoma and condyloma, respectively.

Dosage and Schedules

An effective quantity of the compound of interest is employed in treatment. The dosage of compounds used in accordance with the invention varies depending on the compound and the condition being treated. For example, the age, weight, and clinical condition of the recipient patient; and the experience and judgment of the clinician or practitioner administering the therapy are among the factors affecting the selected dosage. Other factors include: the route of administration, the patient, the patient's medical history, the severity of the disease process, and the potency of the particular compound. The dose should be sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer.

Broadly, for a PPARγ ligand, e.g. a thiazolidinedione such as troglitazone, the oral dose is determined from the following formula:

oral dose (in mg)=$(k_1)(EC_{50[<r]eset)(k_2)})$ (LBW) (MW);

wherein $k_1$ is a dimensionless constant of 5 to 100;

$EC_{50}$ is the concentration (amount) of compound required to activate or bind to 50% of PPARγ in the sample or patient and is in mole/L units;

$k_2$ is the fractional water content of the lean body weight (LBW) of the patient=0.72 L/kg, (see, GEIGY SCIENTIFIC TABLES, VOL. 1, Lentner (ed.), p217, Giba-Geigy Ltd., Basle, Switzerland (1981); and MW is the molecular weight of the compound in g/mole.

For example, troglitazone is a compound encompassed by the methods of this invention. A man with diagnosis of early stage prostate cancer in situ has a lean body weight (LBW) of 70 kg. If $k_1$=10; the $EC_{50}$ for troglitazone=$2.4\times10^{-6}$ mol/L and the molecular weight of troglitazone=442 g/mol, then the oral dose in milligrams=$(10)(2.4\times10^{-6}$ mol/L$)(0.72$ L/kg$\times70$ kg$)$ (442 g/mol) or 535 mg.

Similarly, an effective dose of rosiglitazone in milligrams for an average man is $(10)(0.06\times10^{-6}$ mol/L$)(0.72$L/kg$\times70$ kg$)(304$ g/mole) or 9.2 mg.

Typically, the dosage per day of a thiazolidinedione of this invention will depend on the affinity of the thiazolidinedione for PPARγ. The dosages of compounds with high affinity, e.g., rosiglitazone, will fall between about 0.5 mg to about 100 mg, of compounds of intermediate affinity will fall from about 10 mg to about 500 g and compounds with low affinity, e.g., troglitazone, will fall from about 100 mg to about 5 g.

An oral dosing schedule is typically, a single dose once a day. However, more than one dose can be given per day. Because of the lower incidence of undesirable side effects, the compounds of this invention can be given until improvement in the inflammatory process or disease involving neovascularization is observed.

Because the compounds of this invention are to some degree fat-soluble, in a preferred embodiment, the compounds are administered with food. The fats in food provide a lipid micellular phase in which the PPARγ modifiers of this invention can solubilize and be more effectively absorbed.

A dosage range for local treatment is about 0.1% to about 10% (weight/volume) in a suitable solvent applied that permits release of the compound into the prostate tissue. One of skill will realize that the dosage for local treatment will vary depending on the compound used. For example, the thiazolidinediones of this invention have different affinity for PPARγ, e.g., pioglitazone has a higher affinity for PPARγ than troglitazone. Typically, the greater the affinity, the more effective the compound, and the lower the dosage that is an effective amount. Therefore, a lower concentration of pioglitazone in a unit dosage form comprises an effective amount.

Typically, the local dosage is administered at least once a day until a therapeutic result is achieved. The dosage can be administered twice a day, but more or less frequent dosing can be recommended by the clinician. Once a therapeutic result is achieved, the compound can be tapered or discontinued. Occasionally, side effects warrant discontinuation of therapy.

Combination Therapies with PPARγ Agonists

Combination Therapy with a PPARγ Agonist and Other Nuclear Receptor Ligands

Compounds that bind or modify the activity of PPARγ can also be given by a selected route of administration, e.g. orally or delivered in situ, in combination with compounds that bind or modify the activity of the vitamin D receptor or in combination with compounds that bind or modify the activity of the retinoid X receptors or retinoic acid receptors to provide for a synergistic effect in the treatment or prevention of a specific ocular disease. Examples of such compounds that provide for synergistic effect when given in combination with the compounds encompassed by the current invention include glucocorticoids, vitamin D analogs, retinoic acid derivatives. Examples of ligands for retinoid X receptors include, but not limited to 9-cis-retinoic acid LG100268, tazarotene, TTNPB, LGD1069 (Targretin), and phytannic acid. Examples of retinoic acid receptor ligands are all-trans retinoic acid, tazarotene, etretinate and acitretin.

Methods of achieving synergistic effects for enhanced inhibition of inflammation, proliferation, or prevent apoptosis of cells or tissues constituting the target lesion includes the use of the aforementioned PPARγ ligands in combination with a compound that binds to and or modifies the activity of either the vitamin D receptor or retinoid X receptors or retinoic acid receptors sufficient to inhibit the growth or proliferation or prevent apoptosis of the diseased cells or tissues. A preferred dosage range for administration of a retinoic acid derivative or retinoid would typically be from 0.1 to 100 mg/m$^2$ of body surface area, depending on the compound's ability to bind to or modify the activity of its PPARγ, given in single or divided doses, orally or by continuous infusion, two or three times per day.

Examples of effective retinoids are 9-cis-retinoic acid, 13-cis-retinoic acid, all-trans-retinoic acid (at-RA). Preferred retinoids for this purpose would include 13-cis-retinoic acid, tazarotene, or Targretin. A preferred dosage range for systemic administration of a vitamin D analog would typically be from 0.1 to 100 mg/m$^2$ of body surface area, depending on the compound's ability to bind to and or activate its cognate vitamin D receptor, given in single or divided doses, orally or by continuous infusion, two or three times per day. Some examples of effective vitamin D analogs are 1,25-dihydroxy-vitamin D (1,25-(OH)$_2$-Vit D) and calcipotriol.

Examples of effective glucocorticoids for use in combination with a PPARγ agonist include, are hydrocortisone (low potency, short-acting), prednisolone (intermediate potency, intermediate-acting), or dexarnethasone (high potency, long-acting). Examples of effective non-steroidal anti-inflammatory drugs for use in combination with a PPARγ agonist include diclofenac or ketorolac. Preferred methods of administration are topical or delivered directly in situ. Examples of optical diseases treatable with a PPARγ agonist combined with a glucocorticoid or a non-steroidal anti-inflammatory agent include, conjunctivitis, keratitis, corneal ulcers, herpes zoster ophthalmicus, iritis, iridocyclitis, chorioretinitis, uveitis, choroiditis, optic neuritis, and other forms of ophthalmic inflammatory diseases.

Combination Therapy with a PPARγ Agonist and a Protein Kinase Inhibitors

Methods of achieving synergistic effects for enhanced inhibition of inflammation and/or proliferation of cells or tissues constituting the target lesion includes the use of PPARγ ligands, e.g. a PPARγ agonist, in combination with: 1) inhibitors of the serine/threonine protein kinases, mitogen-activated protein kinase (MAP kinase), MAP kinase kinase (MEK 1) and extracellular-signal-regulated protein kinases (Erks). PD098059 (Parke-Davis) is an example of an inhibitor of these serine/threonine protein kinases. According to this invention, PPARγ agonists is administered in combination with inhibitors of tryosine kinases (e.g. growth factor receptor tyrosine kinases) and inhibitors of protein kinase C. Examples of tyrosine kinase inhibitors include isoflavones such as genistein. Examples of protein kinase C inhibitors include staurosporine and its derivatives, e.g. CGP 41251 (Novartis).

Combination Therapy with a PPARγ Agonist and a Flavonoid

Methods of achieving synergistic effects for enhanced inhibition of inflammation and/or proliferation of cells or tissues constituting the target lesion includes the use of PPARγ ligands, e.g. a PPARγ agonist, in combination with a natural or synthetic flavonoid. Examples of natural flavonoids and polyphenols include, flavones (e.g. quercetin), flavonones, isoflavones (e.g. genistein), flavonols, catechins, epicatechins (e.g. epigallocatechin gallate) cyanidins, proanthocyanidin, anthocyanidins, terpenes, tannins, lutein, luteolin, gingerol, and curcumin, and their glycosides and aglycones.

Combination Therapy with a PPARγ Agonist and an Antioxidant

Methods of achieving synergistic effects for enhanced inhibition of inflammation and/or proliferation of cells or tissues constituting the target lesion includes the use of PPARγ ligands, e.g. a PPARγ agonist, in combination with a natural or synthetic antioxidant. Examples of antioxidants include ascorbic acid (vitamin C), vitamin E, succinylated tocopherols and related tocopherol isomers, α-lipoic acid, carotenes (e.g. lutein, β-carotene), carotenoids (e.g. lutein), N-acetyl-cysteine, selenium and melatonin. Another formulation of this invention includes antioxidant enzymes, including selenium and copper/zinc superoxide dismutases, catalase, glutathione peroxidase, and heme oxygenase-1 and heme oxygenase-2.

Combination Therapy with a PPARγ Agonist and an Anti-infective Agent

Methods of achieving synergistic effects for enhanced inhibition of an inflammatory and/or proliferation of cells or tissues caused by an infectious agent includes the use of PPARγ ligands, e.g. a PPARγ agonist, in combination with an antibiotic or anti-infective agent specific for the invasive organism.

In the case that the etiological (infectious) agent is a virus, the PPARγ is administered in combination with an antiviral specific for the virus, systemically (e.g. intravenously or orally) or delivered in situ, to the target of the disease in a tissue-specific fashion. In the case that cytomegalovirus (CMV) is the infective agent, examples of tissue-specific diseases are CMV retinitis (retina) or CMV keratitis (cornea), and an example of a CMV antiviral drug is gancyclovir. In the case that herpes simplex virus (HSV) is the infective agent, examples of tissue-specific diseases are herpetic keratitis (cornea) and iridocyclitis (iris), and examples of HSV antiviral drugs are acyclovir, famciclovir or valaciclovir.

Ophthalmic diseases related to the human immunodeficiency virus (HIV) includes diseases directly related to the HIV viral infection, such as: HIV-related occlusive vasculitis, HIV-related retinal vasculopathy, HIV-mediated neurodegenerative disease of the retina, progressive outer retinal necrosis, in which a PPARγ agonist is administered in combination with an HIV-specific antiviral agent, e.g. reverse transcriptase inhibitors (zidovudine, lamivudine, zidovudine, stavudine) and/or protease inhibitors (nelfinavir, amprenavir). According to this invention, HIV-related proliferative non-neoplastic (e.g. molluscum contagiosum) and neoplastic (e.g. Kaposi's sarcoma, B cell lymphoma) diseases involving the eye are treatable with a PPARγ agonist being administered in combination with an HIV-specific antiviral agent. Another method of this invention is the treatment of opportunistic ophthalmic infections that occur in high incidence in the context of HIV infection. Examples of these diseases are microsporidial keratoconjunctivitis, herpes zoster ophthalmicus, cytomegalovirus retinitis, toxoplasma retinochorditis, syphylitic chorioretinitis, histoplasmosis, infectious multifocal choroiditis, and drug-induced retinitis (e.g. rifabutin-induced retinitis), can be treated with a PPARγ agonist in combination with HIV-specific antiviral agents.

Similarly, according to this invention, a PPARγ agonist is administered in combination with: an antibacterial drug for treating ocular infections and their sequelae caused by bacteria, an antifungal drug for treating ocular infections and their sequelae caused by fungae, an antiparasitic drug for treating ocular infections and their sequelae caused by parasites.

Combination Therapies with PPARγ Antagonists
Combination Therapy with a PPARγ Antagonist and an Anti-apoptotic Agent As described above, the neuropeptide, bombesin has been shown to inhibit methadone-induced apoptosis of human lung carcinoma cells (Heusch W L, et al. Cancer Lett. 1999; 136:177–185). Moreover, in an undifferentiated cerebellar primitive neuroectodermal tumor cell line, members of the family of bone morphogenetic proteins (BMPs), specifically BMP-2 and BMP-4, have been shown to increase in total cell number due to the attenuation of apoptosis (lantosca M R et al. J Neurosci Res 1999; 56:248–258). Therefore, according to this invention, these anti-apoptotic proteins, when applied locally or in situ in combination with a PPARγ antagonist, have the potential treating diseases of the eye in which inappropriate apoptosis is the pathophysiological mechanism. Examples of these diseases are retinal degenerations involving apoptosis, e.g. retinitis pigmentosa. A preferred method of this invention is to apply these anti-apoptotic proteins in situ or subretinally, to achieve local concentrations of 1 to 100 ng/ml, preferably 5 to 25 ng/ml.
Combination Therapy with a PPARγ Antagonist and a Growth Factor or Mitogen Growth factors and mitogens have the potential of acting synergistically with PPARγ antagonists to attenuate apoptosis in ophthalmologic diseases which involve inappropriate apoptosis as the pathophysiological mechanism. Thus, in another embodiment of this invention administration of one or more of these growth factors in combination with a PPARγ antagonist, when applied locally or in situ is applied in the treatment of these diseases.

Examples of growth factor and/or mitogens effective in the application of this invention include: basic fibroblast growth factor (bFGF), platelet-derived growth factor (PDGF-AA, PDGF-AB or PDGF-BB isoforms), epidermal growth factor (NGF), insulin-like growth factor-1 (IGF-1) and nerve growth factor (NGF). Target diseases are retinal degenerations involving apoptosis, e.g. retinitis pigmentosa. A preferred method of this invention is to apply these anti-apoptotic proteins in situ or subretinally, to achieve local concentrations of 1 to 100 ng/ml, preferably 5 to 25 ng/ml.

Methods of this invention include administering to a human or animal for treatment of an inflammatory or proliferative or neovascular disease involving angiogenesis, an effective amount of a PPARγ agonist, or a PPARγ antagonist in case of dystrophic or degenerative diseases involving apoptosis. The PPARγ agonist may be administered alone or in combination with a RXR activator, a retinoid or vitamin A derivative, a flavonoid, a glucocorticoid, a vitamin D derivative, an arachidonic acid derivative, a nutrient vitamin, an antibiotic, a protein kinase C inhibitor, a MAP kinase inhibitor, or an antioxidant. In the case of apoptosis, the PPARγ antagonist may be administered alone or in combination with a growth factor or mitogen, a MAP kinase activator, a protein kinase C activator, a retinoid or vitamin A derivative, a flavonoid, a glucocorticoid, a nutrient vitamin, an arachidonic acid derivative, or an antioxidant.

An effective quantity of the compound of interest is employed in treatment. The dosage of compounds used in accordance with the invention varies depending on the compound and the condition being treated. The age, lean body weight, total weight, body surface area, and clinical condition of the recipient patient; and the experience and judgment of the clinician or practitioner administering the therapy are among the factors affecting the selected dosage. Other factors include the route of administration the patient, the patient's medical history, the severity of the disease process, and the potency of the particular compound. The dose should be sufficient to ameliorate symptoms or signs of the disease treated without producing unacceptable toxicity to the patient.

Broadly, an oral dosing schedule is from about 1.0 to about 1,000 mg once or twice a day depending on the binding affinity of the compound for PPARγ. For example, the typical oral dose of the thiazolidinedione, troglitazone (Parke-Davis/Sankyo), presently approved for the treatment of type 2 diabetes mellitus, is 400 mg once daily. In contrast, the thiazolidinedione, BRL 49653 (SmithKline Beecham) which has a binding affinity 40 times greater than troglitazone, would have a dosing schedule of 2.0 to 20 mg, more typically 4.0 to 8.0 mg once or twice daily.

Using troglitazone as the prototype agent for the purpose of this invention, a convenient oral dose for an adult patient is 300 to 600 mg once a day. A dosage range for topical treatment is about 0.5% to about 5% (weight/volume) in a gel, cream or ointment, applied twice a day. A usual dose for intraocular injection is 1 to 10 mg, depending on the compartment of the eye to be treated and on the lean body mass of the patient. A typical dosage for intra-dermal administration is about 10 to 50 mg per extraocular injection per site. A typical dosage for intravenous or intramuscular administration in an adult patient would be between 100 and 400 mg per day given in single or divided doses depending on the judgement of the practitioner.

Typically, the dosage is administered at least once a day until a therapeutic result is achieved. Preferably, the dosage is administered twice a day, but more or less frequent dosing can be recommended by the clinician. Once a therapeutic result is achieved, the drug can be tapered or discontinued. Occasionally, side effects warrant discontinuation of therapy. In general, an effective amount of the compound is that which provides either subjective relief of symptoms or an objectively identifiable improvement as noted by the clinician or other qualified observer.

The compounds in this invention can also be given orally in combination with natural or synthetic compounds that bind to or modify the activity of the vitamin D receptor or in combination with compounds that bind to or modify the activity of the retinoid X receptor to provide for a synergistic effect in the treatment or prevention of the disorders listed in Tables 1, 2 and 3. Examples of such compounds that provide for synergistic effect when given in combination with the drugs encompassed by the current invention include vitamin D analogs, various retinoic acid derivatives, and other ligands for retinoid X receptors or retinoic acid receptors including but not limited to compounds such as LG100268, tazarotene, TTNPB, AGN 190121, adapalene or LGD1069 (Targretin).

Synergistic therapeutic effects can be achieved by oral or topical administration of the drugs encompassed in the current invention together with orally, topically or intravenously administered drugs that bind to and modify the activity of either the vitamin D receptor, the retinoid X receptors, or the retinoic acid receptors. A preferred dosage range for administration of a retinoic acid derivative or retinoid would typically be from 0.1 to 100 mg per square-meter of body surface area, depending on the drug's ability to bind to or modify the activity of its cognate nuclear receptor, given in single or divided doses, orally or by continuous infusion, two or three times per day. For synergistic therapy, the preferred dosages and routes and frequency of administration of the vitamin D analogs or retinoid compounds can be similar to the dosages and routes and frequency of administration ordinarily recommended for these agents when given without PPARγ activators. Examples of effective retinoids are 9-cis-retinoic acid, 13-cis-retinoic acid, all-trans-retinoic acid (at-RA). Preferred retinoids for this purpose would include 13-cis-retinoic acid, tazarotene, or Targretin. A preferred dosage range for systemic administration of a vitamin D analog would typically be from 0.1 to 100 mg per square-meter of body surface area, depending on the drug's ability to bind to and or activate its cognate vitamin D receptor, given in single or divided doses, orally or by continuous infusion, two or three times per day. Examples of effective vitamin D analogs are 1,25-dihydroxy-vitamin D, calcipotriene and calcipotriol. The dosage range and routes and frequency of administration of PPARγ activators required to achieve synergistic effects when given with vitamin D or retinoid derivatives are the same as those described elsewhere in this disclosure. The preferred mode of administration of these drugs for synergistic therapeutic purposes would be orally although alternatively one can use topical or parenteral routes of administration. The dosages and the modes and frequency of administration of the vitamin D or retinoid related compounds for synergistic topical therapy would be similar to those ordinarily recommended for these agents when given without PPARγ activators. The dosage range and the modes and frequency required for topical administration of the flavonoid thiazolidine derivatives given in combination with vitamin D or retinoid related compounds are the same as those described elsewhere in this disclosure.

Synergistic therapeutic effects can be achieved by oral or topical administration of the drugs encompassed in the current invention together with orally, topically or intravenously administered natural or synthetic antioxidants. These include ascorbic acid and its derivatives (e.g. vitamin C), the tocopherols (e.g. vitamin E, vitamin E succinate), carotenes and carotenoids (e.g. beta-carotene), alpha-lipoic acid, probucols, flavones, isoflavones and flavonols (e.g. quercetin, genistein, catechin, apigenin, lutein, luteolin), glutathione and its derivatives (e.g. N-acetylcysteine and dithiothreitol), and phytoestrogens and phenolic anthocyanidin and procyanidin derivatives (e.g. resveratrol, cyanidin, cinnamic acid).

EXAMPLES OF HOW TO PRACTICE THE INVENTION

Example 1

Treatment of Retinitis Pigmentosa OR Macular Degeneration by Oral Administration of Troglitazone - A Clinical Trial Early disease: A patient having early ophthalmic manifestations of retinitis pigmentosa is selected for therapy. The patient weighs 70 kilograms, and if female of child-bearing capacity, is given a pregnancy test to confirm that she is not pregnant. Provided that the patient is not pregnant and does not plan to become pregnant during treatment, a compound known to activate PPARγ, namely, the thiazolidinedione, troglitazone is administered orally in a dosage of 400 milligrams daily with a fat-containing meal. The patient is evaluated by an ophthalmologist experienced in the ophthalmic manifestations of retinitis pigmentosa lesions. Regression of the disease or improvement in his clinical status is evaluated by monitoring the visual fields. Additionally, a complete blood count, including white cell count and differential, a platelet count, and liver function tests (such as levels of alkaline phosphatase, lactate dehydrogenase, and aminotransferases) are checked prior to treatment and monthly thereafter. The dosage is tapered to a maintenance dose of 200 mg.

Late disease: A similar patient with late ophthalmic manifestations of retinitis pigmentosa is selected for therapy. The approach is the same as for the foregoing patient, except that the starting dose of 400 mg troglitazone once daily is increased progressively by 200 mg at 8 wk intervals to 800 mg. After 12 months at 800 mg, the dose is decreased to 600 mg for an additional 12 months then to a maintenance dose of 400 mg once daily.

Example 2

Treatment of Retinitis Pigmentosa OR Macular Degeneration by Oral Administration of Rosiglitazone (BRL 49653)—A Clinical Trial Early disease: A patient having early ophthalmic manifestations of retinitis pigmentosa is selected for therapy. The patient weighs 70 kilograms, and if female of child-bearing capacity, is given a pregnancy test to confirm that she is not pregnant. Provided that the patient is not pregnant and does not plan to become pregnant during treatment, a compound known to activate PPARγ, namely, the thiazolidinedione, rosiglitazone (BRL 49653) is administered orally in a dosage of 8 milligrams daily with a fat-containing meal. The patient is evaluated by an ophthalmologist experienced in the ophthalmic manifestations of retinitis pigmentosa lesions. Regression of the disease or improvement in his clinical status is evaluated by monitoring the visual fields. Additionally, a complete blood count, including white cell count and differential, a platelet count, and liver function tests (such as levels of alkaline phosphatase, lactate dehydrogenase, and aminotransferases) are checked prior to treatment and monthly thereafter. The dosage is tapered to a maintenance dose of 4 mg.

Late disease: A similar patient with late ophthalmic manifestations of retinitis pigmentosa is selected for therapy. The approach is the same as for the foregoing patient, except that the starting dose of 8 mg rosiglitazone once daily is increased progressively by 4 mg at 8 wk intervals to 16 mg. After 12 months at 20 mg, the dose is decreased to 12 mg for an additional 12 months then to a maintenance dose of 8 mg once daily.

TABLE 1

Inflammatory ocular diseases treatable with PPARγ ligands

| Disease Category | Examples of Disease Types, Causes Associated Conditions |
| --- | --- |
| Conjunctivitis: | Allergic c., chronic c., contact lens-associated c. conjunctival ulceration, drug-related c. |
| Uveitis, Uveoretinitis, Panuveitis, Retinitis, Choroiditis, Vitreitis, Scleritis/Episcleritis, Iridocyclitis, Endophthalmitis | Chronic diseases (e.g. age-related macular degeneration diabetes mellitus, infectious diseases (e.g., tuberculosis syphilis, cytomegalovirus retinitis), physical agents (e.g. UV radiation), chemical agents (e.g. acids, caustic solvents) immunological etiologies (e.g. sarcoidosis, inflammatory bowel Corneal ulceration disease, other collagen vascular diseases) |

TABLE 2

Non-hereditary degenerative diseases treatable with PPARγ ligands

| | |
| --- | --- |
| Macular disorders: | All etiologies and manifestations, including age-related macular degeneration, exudative macular degeneration, atrophic macular degeneration, crystalline retinopathies, retinal toxicosis of systemic medications, idiopathic central serous choroidiopathy, macular edema |
| Retinovascular diseases and retinopathies: | Retinopathy, vasculo-occlusive r., idiopathic r., hypertensive r., proliferative r., diabetic r., vitreoretinopathy, vasculopathies associated with telangiectasias or aneurysms, retinopathies associated with lupus erythematosus, rheumatoid arthritis, multiple sclerosis, myasthenia gravis, uveoretinitis or diabetes mellitus |
| Glaucoma: | All etiologies and manifestations, including primary and secondary open-angle glaucoma, angle-closure glaucoma, glaucoma associated with intraocular inflammation, steriod-induced glaucoma, glaucoma associated with intraocular hemorrhage, pseudoexfoliative syndrome, glaucomatous optic neuropathy |
| Cataract: | All etiologies and manifestations, including age-related (UV radiation) cataract, cataract associated with systemic diseases such as collagen vascular disease, diabetes mellitus, Wilson's disease |
| Other diseases: | Primary or secondary retinal detachment |

TABLE 3

Hereditary degenerative retinal and vitreoretinal diseases treatable with PPARγ ligands

1. Primary pigmented retinopathies, all gene types (ocular involvement only)

Autosomal dominant retinitis pigmentosa
   e.g. rod-cone and cone-rod degenerations
   Autosomal recessive retinitis pigmentosa
   e.g. rod-cone and cone-rode degenerations, Lerner's amaurosis congenita
   X-linked recessive pigmented retinopathies
   e.g. choroideremia 2. Secondary pigmented retinopathies (retinopathies associated with systemic diseases)

Autosomal dominant pigmented retinopathies
   e.g. Paget's d., Charcot-Marie-Tooth d., Steinert's d., Pierre-Marie syndrome
   Autosomal dominant pigmented retinopathies
   e.g. diabetes mellitus, mannosidoses, mucopolysccharidoses, Batten's d., Refsum's d., Usher syndrome
   X-linked recessive pigmented retinopathies
   e.g. Hunter syndrome

Preparation and Ophthalmic Uses of Novel Compounds

A further aspect of the present invention involves novel compounds, their synthesis, and use in the treatment of ophthalmic disorders. In one aspect, the present invention is directed to the making of a compound having the general structure A set forth below:

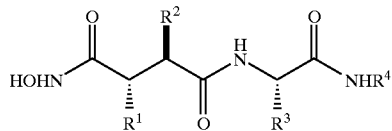

wherein $R^1$ is OH, $OXR^6$, OY, or

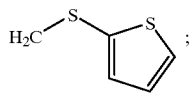

$R_2$ is $C_1$–$C_8$ alkyl, aryl, alkaryl or arylalkyl where aryl groups are defined as substituted or unsubstituted phenyl, biphenyl, naphthyl or pyridyl groups; $R^3$ is $CH_2R^5$, $C_1$–$C_8$ alkyl, aryl, alkaryl or arylalkyl where aryl groups are defined as substituted or unsubstituted phenyl, biphenyl, naphthyl or pyridyl groups; $R^4$ is H, $XR^6$, or Y; $R^5$ is the residue of a naturally occurring amino acid;

$R^6$ is

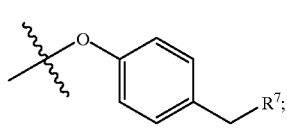

$R^7$ is

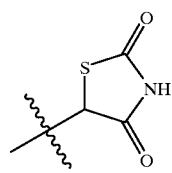

or

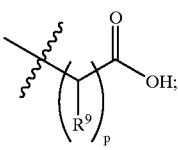

$R^9$ is

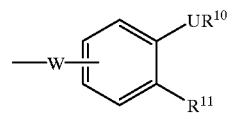

or —W—$R^{17}$; $R^{10}$ is $(CH_2)_q$—$R^{12}$, $NH_2$, NHMe, $NMe_2$, $OR^{18}$, ($C_3$–$C_8$)cycloalkyl, or unsubstituted, monosubstituted or disubstituted Ar; $R^{11}$ and $R^{13}$ are either hydrogen or combine to form a single bond or, alternately, $R^{13}$ is U and $R^{11}$ forms a direct link with U to form a single bond;

$R^{12}$ is either

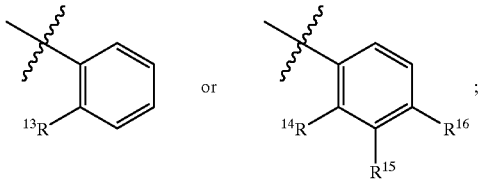

$R^{14}$, $R^{15}$ and $R^{16}$ are independently hydrogen, $CF_3$, ($C_1$–$C_6$) alkyl, ($C_1$–$C_6$)alkoxy, Ar or Ar—$(CH_2)_t$—O—; $R^{17}$ is unsubstituted, monosubstituted or disubstituted Ar; $R^{18}$ is hydrogen or ($C_1$–$C_6$)alkyl; each U is independently $CH_2$, CHOH, C=O, O, S, SO, $SO_2$, C=N—$NH_2$; W is O, S, NH, or $CH_2$; X is —$(CH_2)_n$— or —$(CH_2)_n$—NY—$(CH_2)_o$—;

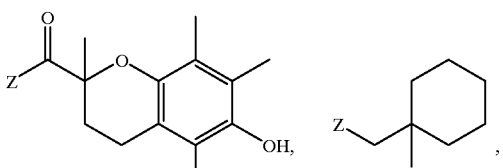

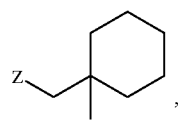

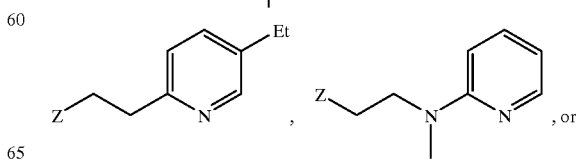

Y is

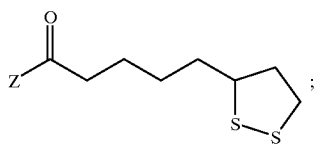

Z is a direct link, A—(CH$_2$)$_n$—NH—, or A—(CH$_2$)$_n$—O—;
A is a direct link; n=2–10; o=2–10; p is an integer from 0 to 1; q is an integer from 0 to 6; and t is an integer from 1 to 6; wherein if R$_1$ is H then R$_4$ is XR$_6$ where X is —(CH$_2$)$_n$—NY—(CH$_2$)$_o$—; if R$_1$ is Y then R$_4$ is XR$_6$ where X is —(CH$_2$)$_n$—; if R$_4$ is H then R$_1$ is XR$_6$ where X is —(CH$_2$)$_n$—NY—(CH$_2$)$_o$—; and if R$_4$ is Y then R$_1$ is XR$_6$ where X is —(CH$_2$)$_n$—. Preferred embodiments of the present invention include the following thiazolidinediones, which are referred to as Example 1, Example 2, Example 3, and Example 4:

Example 1

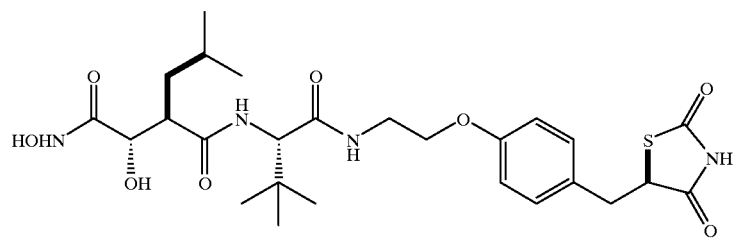

Example 2

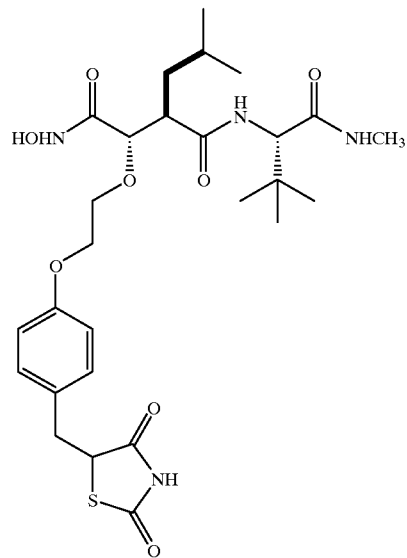

Example 3

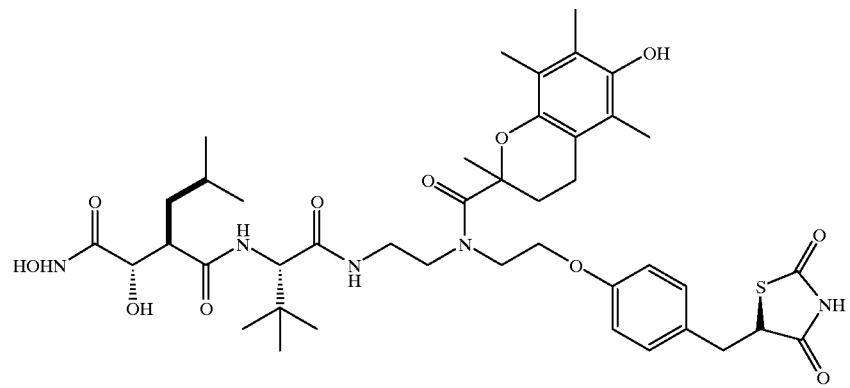

Example 4

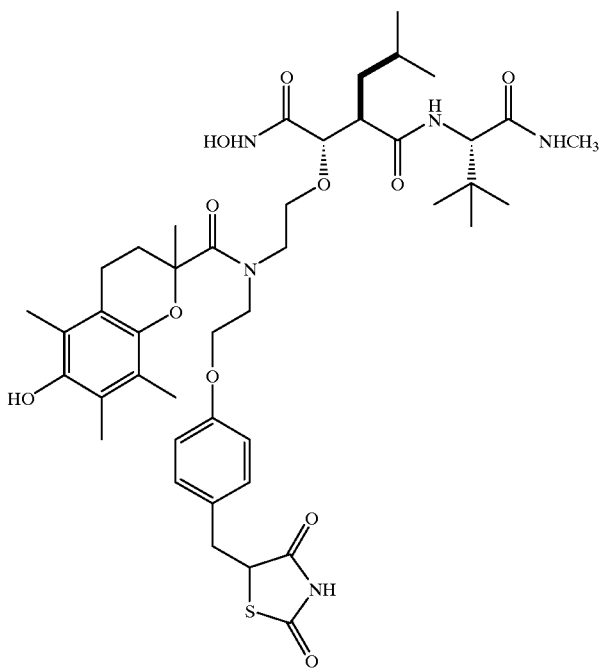

For each of the compounds labeled below as Example 1, Example 2, Example 3, and Example 4, the corresponding synthetic schemes are illustrated on separate pages respectively having the corresponding title. The compounds (e.g., Compound 1) referred to in the description below are shown in the respective synthetic scheme illustration. In a preferred embodiment, these compounds exhibit MMPI activity, as well as PPARγ activity, and are administered in an effective amount to a mammal in need thereof to treat at least one ophthalmic disease set forth herein.

Synthesis of the Compound of Example 1

With reference to the page headed by the title EXAMPLE 1, Compound 1 is prepared from tyrosine according to procedures reported by Arakawa, et al (See Chem. Pharm. Bull., 1997, 45(12), 1984–1993). Compound 2 is prepared by combining bromoethanol, cesium carbonate and compound 1 in acetonitrile. After stirring at room temperature until the reaction is complete, as demonstrated by TLC analysis, the reaction is concentrated. The product is isolated from the resulting residue by partitioning between ethyl acetate and brine. The ethyl acetate layer is dried over anhydrous magnesium sulfate, filtered and concentrated. The residue can be purified utilizing silica gel chromatography.

Compound 3 is prepared by first reacting compound 2 with methanesulfonyl chloride in the presence of triethylamine utilizing methylene chloride as the solvent. The resulting crude product is dissolved in dimethyl formamide and sodium azide is added. The reaction is stirred at 50 deg C until complete by TLC analysis. The product is isolated by pouring the reaction mixture onto water and filtering the resulting precipitate. This product can be purified utilizing silica gel chromatography. Following purification, the resulting azide is converted to the corresponding amine on treatment with triphenylphosphine and water (this procedure is much milder than utilization of lithium aluminum hydride and the thiazolidine dione would be expected to remain intact).

Compound 4 is prepared as described in Levy, et al., (See Journal of Medicinal Chemistry, 1998, 41(2), 199–223) (compound 1n). Compound 5 is prepared by combining compounds 3 and 4 as described by Levy, et al.,(general procedures D and E). Compound 6 is prepared according to Levy, et al., (sequential preparation of compounds 23, 24, 25 and 26). Compound 7 is prepared by combining compounds 5 and 6 according to Levy, et al., utilizing procedures analogous to the sequential preparation of compounds 27b and 7f. Compound 8 is prepared from compound 7 according to Levy, et al., utilizing procedures analogous to the sequential preparation of compounds 5ooo and 6kkk (General procedure G).

Synthesis of the Compound of Example 2

With reference to the page headed by the title EXAMPLE 2, Compound 9 is prepared by treating compound 2 with carbon tetrabromide in the presence of triphenylphosphine utilizing dichloromethane as the solvent. The product can be purified utilizing silica gel chromatography.

Compound 10 is prepared by treating compound 6 with benzyl bromide in the presence of potassium carbonate utilizing methanol or dimethylformamide as the solvent. The resulting benzyl ester is reacted under acidic conditions according to Levy, et al., (compound 19). The resulting carboxylic acid is converted to the corresponding methyl ester utilizing conditions according to Levy, et al., (compound 5ooo).

Compound 11 is prepared by combining compounds 9 and 10 according to Levy, et al.,[2] (compound 21a or 21b). The resulting product is converted to a carboxylic acid according to Levy, et al., (compound 4g or 4h). Compound 12 is prepared as described by Levy, et al., (sequential preparation of compounds 2aaa and 3aaa).

Compound 13 is prepared by combining compounds 11 and 12 according to Levy, et al., (general procedure F). Compound 14 is prepared from compound 13 according to Levy, et al., utilizing a procedure analogous to the preparation of compound 6kkk (General procedure G).

Synthesis of the Compound of Example 3

With reference to the page headed by the title EXAMPLE 3, Compound 16 is prepared by first treating ethylene glycol (compound 15) with one equivalent of tert-butyl dimethyl chlorosilane and imidazole. Subsequent application of the Swern oxidation (See Synthesis, 1981, 165–185) provides the final aldehyde. Compound 18 is prepared by combining compound 16 and compound 17 (commercially available) in aqueous saturated sodium bicarbonate solution followed by addition of sodium cyanoborohydride. Compound 19 is prepared by first treating compound 18 with benzyl chloroformate in a solution of aqueous saturated sodium bicarbonate. The tert-butyl dimethylsilyl group is then removed utilizing a solution of tetrabutyl ammonium fluoride in tetrahydrofuran. The resulting alcohol is then combined with triphenylphosphine in methylene chloride and cooled to 0 deg C. To the cooled solution is added a solution of carbon tetrabromide in methylene chloride.

Compound 20 is prepared by combining compound 19, cesium carbonate and compound 1 in acetonitrile. After stirring at room temperature until the reaction is complete, as demonstrated by TLC analysis, the reaction is concentrated. The product is isolated from the resulting residue by partitioning between ethyl acetate and brine. The ethyl acetate layer is dried over anhydrous magnesium sulfate, filtered and concentrated. The residue can be purified utilizing silica gel chromatography. The resulting product is dissolved in methanol and added to a suspension of 10% Pd/C in methanol. The resulting mixture is shaken under a hydrogen atmosphere (40 psi). After the reaction is complete by TLC analysis, the solids are filtered and the filtrate is concentrated giving the secondary amine. Compound 22 is prepared from compounds 20 and 21 as described by Levy, et al., (general procedures D and E). Compound 23 is prepared from compounds 4 and 22 as described by Levy, et al., (general procedures D and E). Compound 24 is prepared from compounds 6 and 23 as described by Levy, et al., (general procedures D and E followed by the procedures used for the preparation of compounds 5ooo and 6kkk).

Synthesis of the Compound of Example 4

With reference to the page headed by the title EXAMPLE 4, Compound 25 is prepared from compound 21 and diethanolamine as described by Levy, et al., (general procedures D and E).

Compound 26 is prepared by first treating compound 25 with one equivalent of tert-butyl dimethyl chlorosilane and imidazole. The alcohol is then combined with triphenylphosphine in methylene chloride and cooled to 0 deg C. To the cooled solution is added a solution of carbon tetrabromide in methylene chloride.

Compound 27 is prepared by combining compound 26, cesium carbonate and compound 1 in acetonitrile. After stirring at room temperature until the reaction is complete, as demonstrated by TLC analysis, the reaction is concentrated. The product is isolated from the resulting residue by partitioning between ethyl acetate and brine. The ethyl acetate layer is dried over anhydrous magnesium sulfate, filtered and concentrated. The residue can be purified utilizing silica gel chromatography. The tert-butyl dimethylsilyl group is then removed utilizing a solution of tetrabutyl ammonium fluoride in tetrahydrofuran. The resulting alcohol is then combined with triphenylphosphine in methylene chloride and cooled to 0 deg C. To the cooled solution is added a solution of carbon tetrabromide in methylene chloride.

Compound 28 is prepared by combining compounds 10 and 27 according to Levy, et al., (compound 21a or 21b). The resulting product is dissolved in methanol and added to a suspension of 10% Pd/C in methanol. The resulting mixture is shaken under a hydrogen atmosphere (40 psi). After the reaction is complete by TLC analysis, the solids are filtered and the filtrate is concentrated giving the desired carboxylic acid.

Compound 29 is prepared by combining compounds 28 and 12 according to Levy, et al., (general procedure F). Compound 30 is prepared from compound 29 according to Levy, et al., utilizing a procedure analogous to the preparation of compound 6kkk (General procedure G).

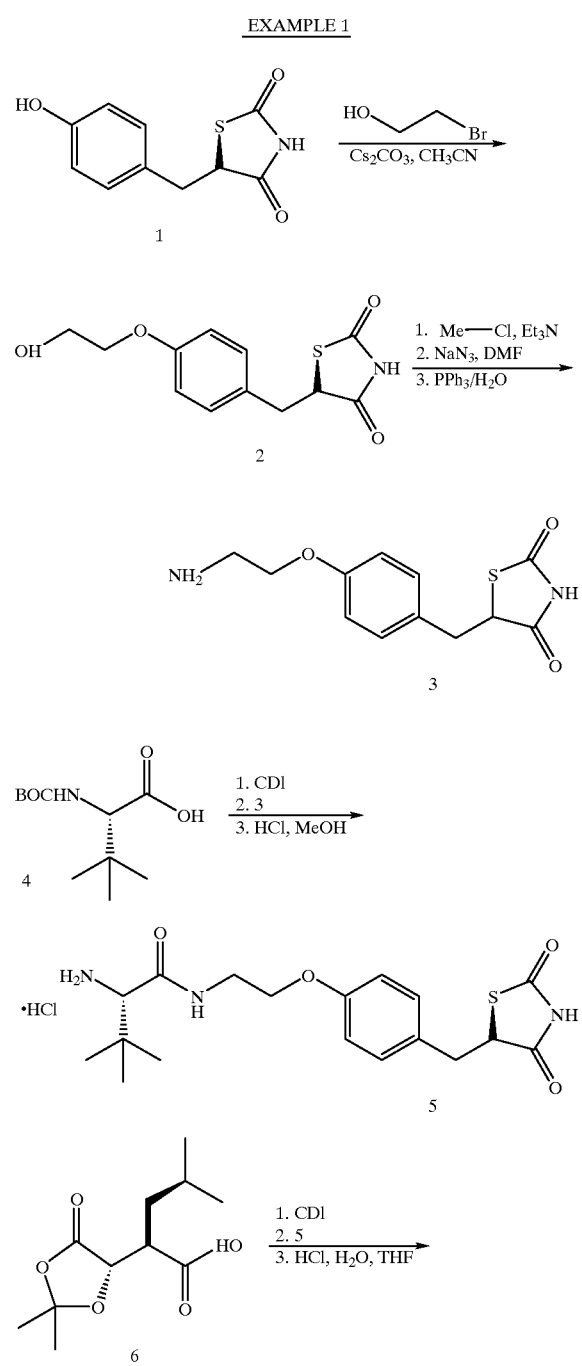

EXAMPLE 1

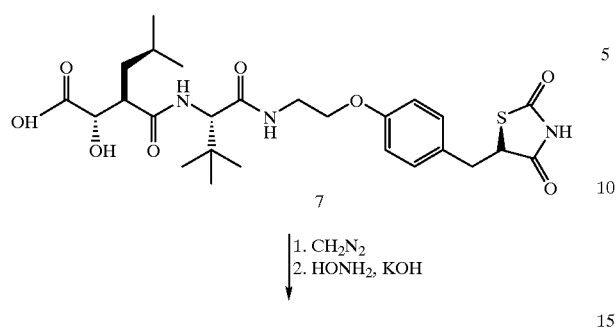
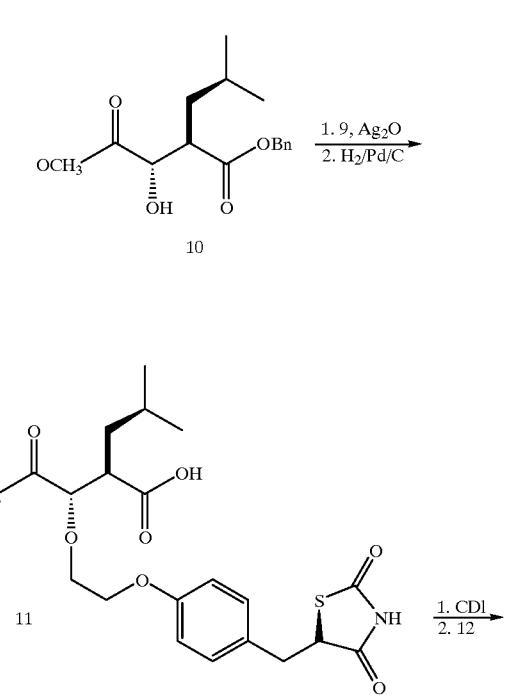
EXAMPLE 2
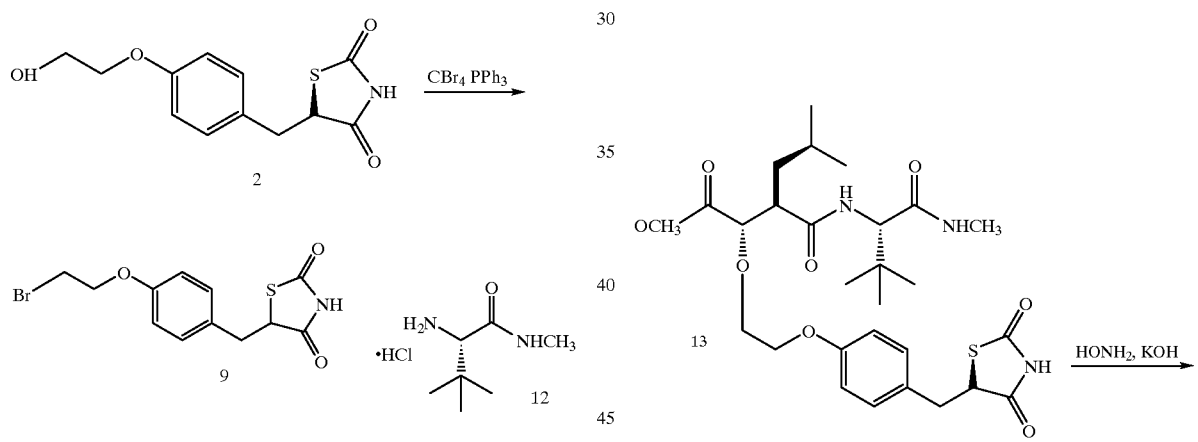
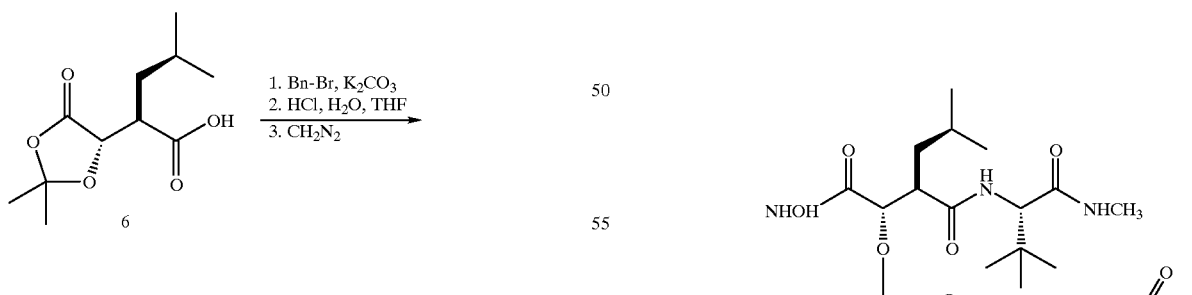
EXAMPLE 3
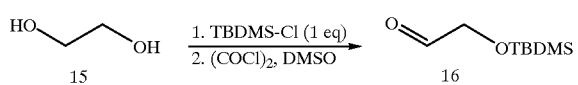

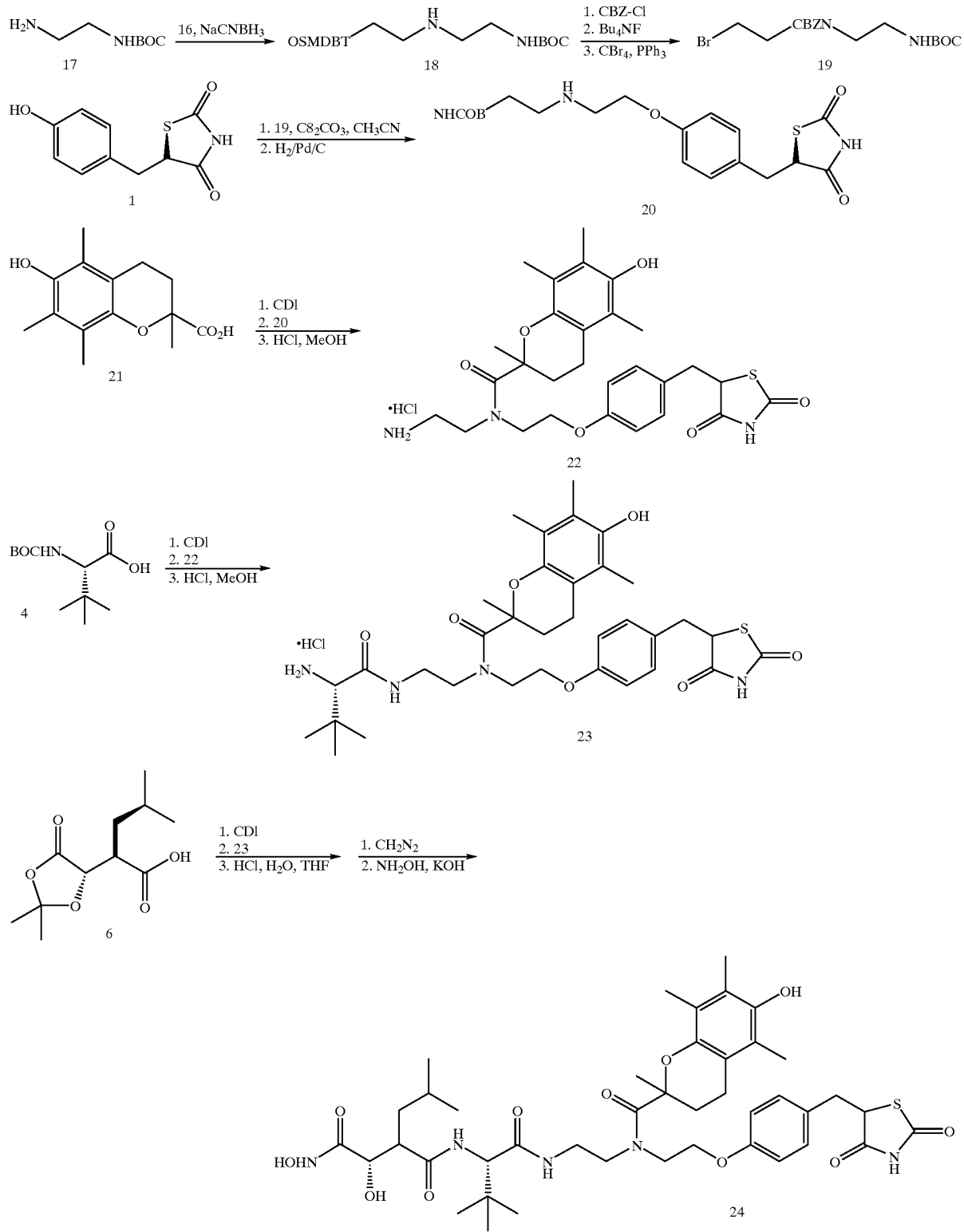

EXAMPLE 4
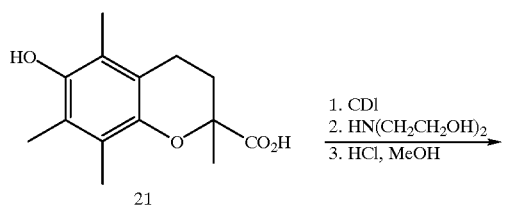
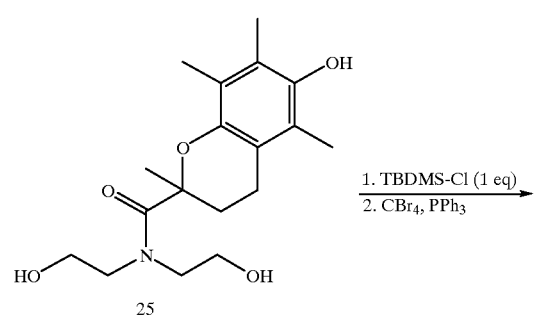
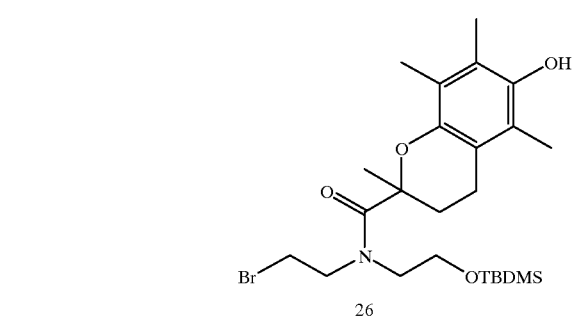
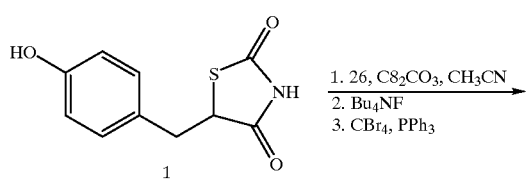
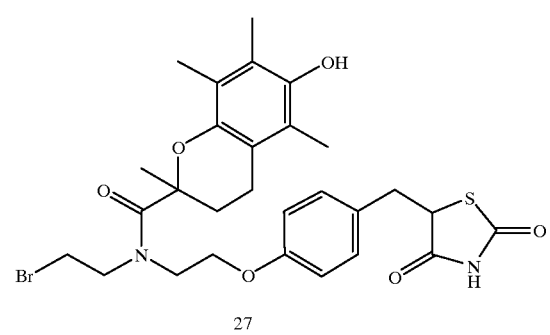
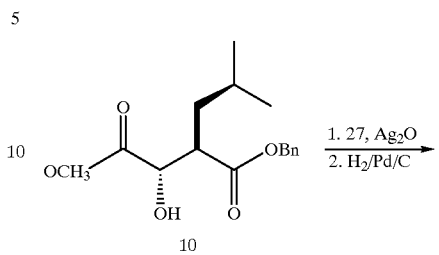
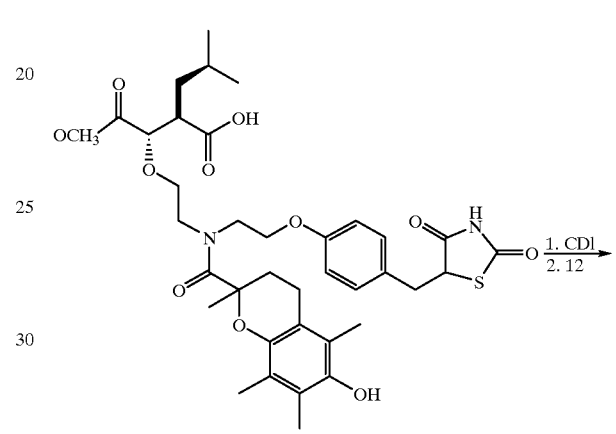
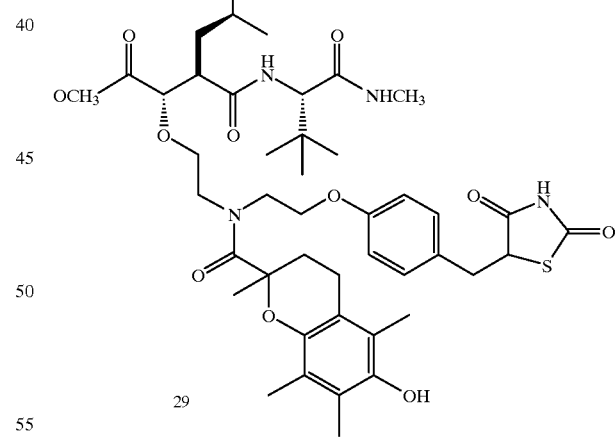
29 →(HONH₂, KOH)

-continued

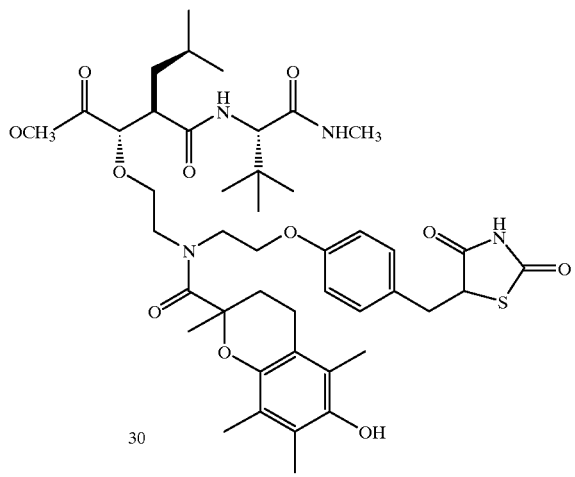

The foregoing is offered primarily for purposes of illustration. It will be readily apparent to those of ordinary skill in the art that the operating conditions, materials, procedural steps and other parameters of the invention described herein may be further modified or substituted in various ways without departing from the spirit and scope of the invention. For example, the invention has been described with human patients as the usual recipient, but veterinary use is also contemplated. Thus, the preceding description of the invention should not be viewed as limiting but as merely exemplary.

What is claimed is:

1. A method of treating inflammatory diseases of the mammalian eye, comprising the step of administering to a human or an animal in need thereof an amount of a PPARγ agonist effective to reverse, slow, stop, or prevent the pathological inflammatory process, wherein the PPARγ agonist is selected from the group consisting of a thiazolidinedione, an N-(2-benzoylphenyl)-L-tyrosine derivative, and an arachidonic acid metabolite.

2. The method of claim 1, wherein the PPARγ agonist is a thiazolidinedione selected from the group consisting of troglitazone, pioglitazone, rosiglitazone, ciglitazone, englitazone, and darglitazone.

3. The method of claim 1, wherein the arachidonic acid metabolite is prostaglandin J2 or PG J2 metabolites.

4. The method of claim 3, wherein a prostaglandin J2 metabolite is 15-deoxy-Δ-12,14-prostaglandin J2.

5. The method of claim 1, further comprising the step of administering a natural or synthetic RXR agonist.

6. The method of claim 5, wherein the RXR agonist is 9-cis-retinoic acid.

7. The method of claim 1, wherein the inflammatory disease involves the retina, uveal tract, cornea or conjunctiva, and the neovascular proliferative disease involves the retina, uveal tract or cornea.

8. The method of claim 1, wherein the inflammatory disease is selected from the group consisting of uveitis, uveoretinitis, panuveitis, retinitis, iridocyclitis, immunological endophthalmitis, choroiditis, vitreitis, keratitis, corneal ulceration, age-related macular degeneration, glaucoma, conjunctivitis, and conjunctival ulceration, and the neovascular proliferative disease is selected from the group consisting of age-related macular degeneration, exudative macular degeneration, atrophic macular degeneration, crystalline retinopathy, retinal toxicosis of systemic medications, idiopathic central serous choroidopathy, macular edema.

9. The method of claim 1, wherein the disease is a retinovascular disease or retinopathy.

10. The method of claim 9, wherein the retinopathy is vasculo-occlusive or idiopathic or a vitreoretinopathy or vasculopathy, or associated with telangiectasias or aneurysms, or associated with lupus erythematosus, rheumatoid arthritis, multiple sclerosis, myasthenia gravis, uveoretinitis or diabetes mellitus, or associated with intraocular surgery or primary or secondary retinal detachment resulting from a disease or injury.

11. A method of treating mammalian ocular diseases involving angiogenesis and proliferative neovascularization, comprising the step of administering to a human or an animal in need thereof an amount of a PPARγ agonist effective to reverse, slow, stop, or prevent a neovascular or proliferative process, wherein the PPARγ agonist is selected from the group consisting of a thiazolidinedione, an N-(2-benzoylphenyl)-L-tyrosine derivative and an arachidonic acid metabolite.

12. The method of claim 11, wherein the PPARγ agonist is a thiazolidinedione selected from the group consisting of troglitazone, pioglitazone, rosiglitazone, ciglitazone, englitazone, and darglitazone.

* * * * *